(12) United States Patent
Contreras et al.

(10) Patent No.: US 7,507,573 B2
(45) Date of Patent: Mar. 24, 2009

(54) MODIFICATION OF PROTEIN GLYCOSYLATION IN METHYLOTROPHIC YEAST

(75) Inventors: Roland Contreras, Merelbeke (BE); Nico L. M. Callewaert, Lichtervelde (BE); Wouter Vervecken, Ghent-Ledeberg (BE); Vladimir Kaigorodov, Ghent (BE)

(73) Assignees: VIB, vzw (BE); Universiteit Gent (BE); Research Corporation Technologies, Inc., Tucson, AZ (US)

( * ) Notice: Subject to any disclaimer, the term of this patent is extended or adjusted under 35 U.S.C. 154(b) by 191 days.

(21) Appl. No.: 10/713,970

(22) Filed: Nov. 14, 2003

(65) Prior Publication Data
US 2005/0106664 A1 May 19, 2005

(51) Int. Cl.
C12Q 1/68 (2006.01)
C12N 15/04 (2006.01)
C12P 21/00 (2006.01)
C12P 19/18 (2006.01)
C12P 1/02 (2006.01)

(52) U.S. Cl. .................. 435/254.11; 435/183; 435/193; 435/227; 435/203; 435/254.23; 435/254.6; 435/71.1

(58) Field of Classification Search .................. 435/6, 435/193, 254.2, 254.11, 254.23, 320.1; 536/23.2
See application file for complete search history.

(56) References Cited

U.S. PATENT DOCUMENTS

| 5,135,854 | A | 8/1992 | MacKay et al. |
| 5,705,616 | A | 1/1998 | Lehle et al. |
| 6,803,225 | B2 | 10/2004 | Contreras et al. |
| 7,029,872 | B2 * | 4/2006 | Gerngross .................. 435/69.1 |
| 2002/0137134 | A1 | 9/2002 | Gerngross | |

FOREIGN PATENT DOCUMENTS

| EP | 0 314 096 | | 5/1989 |
| EP | 0 548 012 | A1 | 6/1993 |
| EP | 0 582 244 | A2 | 2/1994 |
| EP | 1 211 310 | A1 | 6/2002 |
| JP | 8-336387 | | 12/1996 |
| WO | WO 91/05057 | | 4/1991 |
| WO | WO 92/09694 | | 6/1992 |
| WO | WO 96/21038 | | 7/1996 |
| WO | WO 02/00856 | A2 | 1/2002 |
| WO | WO 02/00879 | A2 | 1/2002 |
| WO | WO 03/056914 | A1 | 7/2003 |
| WO | WO 2004/074499 | A2 | 9/2004 |
| WO | WO 2005/100584 | A2 | 10/2005 |

OTHER PUBLICATIONS

Maras, M., et al., "Molecular Cloning and Enzymatic Characterization of a *Trichoderma reesei*, 1, 2—α-D-Mannosidase", *Journal of Biotechnology* vol. 77, No. 2-3, pp. 255-263 (2000).
Bretthauer, R. K., et al., "Glycosylation of *Pichia pastoris*-derived Proteins", *Biotechnol. Appl Biochem*, vol. 30, pp. 193-200 (1999).
Kukuruzinska, M. A., et al., "Protein Glycosylation in Yeast", *Ann. Rev. Biochem.* vol. 56, pp. 915-944 (1987).
Chiba, Y., et al., "Production of Human Compatible High Mannose-Type ($Man_5GlcNAc_2$) Sugar Chains in *Saccharomyces cerevisiae*", *The Journal of Biological Chemistry*, vol. 273, No. 41, pp. 26298-26304 (1998).
Maras, M., et al., In Vivo Synthesis of Complex N-Glycans by Expression of Human N-Acetylglucosaminyltransferase I in the Filamentous Fungus *Trichoderma reesei*, *FEBS Letters*, vol. 452, pp. 365-370 (1999).
Nakanishi-Shindo, Y., et al., "Structure of the N-Linked Oligosaccharides That Show the Complete Loss of α-1,6-Polymannose Outer Chain from *och1*, *och1 mnn1*, and *och1 mnn1 alg3* Mutants of *Saccharomyces cerevisiae*", *The Journal of Biological Chemistry*, vol. 268, No. 35, pp. 26338-26345 (1993).
Martinet, W., et al., "Modification of the Protein Glycosylation Pathway in the Methylotrophic Yeast *Pichia pastoris*", *Biotechnology Letters*, vol. 20, No. 12, pp. 1171-1177 (1998).
Maras, M., et al., "In vitro Conversion of the Carbohydrate Moiety of Fungal Glycoproteins to Mammalian-Type Oligosaccharides", *Eur. J. Biochem.*, vol. 249, pp. 701-707 (1997).
Laroy, W., et al., "Cloning of *Trypanosoma cruzi trans*-Sialidase and Expression in *Pichia pastoris*", *Protein Expression and Purification*, vol. 20, pp. 389-393 (2000).
Inoue, T., et al., "Molecular Cloning and Nucleotide Sequence of the 1,2-a-D-Mannosidase Gene, *msdS*, from *Aspergillus saitoi* and Expression of the Gene in Yeast Cells" *Biochimica et Biophysica Acta*, vol. 1253, pp. 141-145 (1995).
Herscovics, A., et al., "Isolation of a Mouse Golgi Mannosidase cDNA, a Member of a Gene Family Conserved from Yeast to Mammals", *The Journal of Biological Chemistry*, vol. 269, No. 13, pp. 9864-9871 (1994).
Lal, A., et al., "Isolation and Expression of Murine and Rabbit cDNAs Encoding an a1,2-Mannosidase Involved in the Processing of Asparagines-linked Oligosaccharides", *The Journal of Biological Chemistry*, vol. 269, No. 13, pp. 9872-9881 (1994).

(Continued)

*Primary Examiner*—Andrew D Kosar
*Assistant Examiner*—Kagnew H Gebreyesus
(74) *Attorney, Agent, or Firm*—Scully, Scott, Murphy & Presser, P.C.

(57) ABSTRACT

The present invention relates to methods and genetically engineered methylotrophic yeast strains for producing glycoproteins with mammalian-like glycosylation. The present invention also relates to vectors useful for generating methylotrophic yeast strains capable of producing glycoproteins with mammalian-like glycosylation. Glycoproteins produced from the genetically engineered methylotrophic yeast strains are also provided.

20 Claims, 5 Drawing Sheets

OTHER PUBLICATIONS

Trombetta, E.S., et al., "Endoplasmic Recticulum Glucosidase II is Composed of a Catalytic Subunit, Conserved from Yeast to Mammals, and a Tightly Bound Noncatalytic HDEL-containing Subunit", *The Journal of Biological Chemistry*, vol. 271, No. 44, pp. 27509-27516 (1996).

Ngo, J.T., et al., "Computational Complexity, Protein Structure Prediction, and the Levinthal Paradox", *The Protein Folding Problem and Tertiary Structure Prediction*, pp. 491-495 (1994).

Rudinger, J., "Characteristics of the Amino Acids as Components of a Peptide Hormone Sequence", In: Peptide Hormones (Parsons, J.A., Ed.), University Park Press, Baltimore, pp. 1-7 (1976).

*Invitrogen Catalog*, "Yeast Expression", p. 22. (1998).

Cregg, J.M., et al., "High-Level Expression and Efficient Assembly of Hepatitis B Surface Antigen in the Methylotrophic Yeast, *Pichia pastoris*", *Biotechnology*, vol. 5, pp. 479-485 (1987).

Lehle, L., et al., "Glycoprotein Biosynthesis in *Saccharomyces cerevisiae: ngd29*, an *N*-glycosylation Mutant Allelic to *och*1 having a Defect in the Initiation of Outer Chain Formation", *Federation of European Biochemical Societies*, vol. 370, No. 1/2, pp. 41-45 (1995).

Yoko-o, T., et al., "*Schizosaccharomyces pombe och*1+ Encodes αa-1,6-mannosyltransferase that is Involved in Outer Chain Elongation of N-linked Oligosaccharides", *Federation of European Biochemical Societies*, vol. 489, No. 1, pp. 75-80 (2001).

Lal, A., et al., "Substrate Specificities of Recombinant Murine Golgi α1,2-mannosidases IA and IB and Comparison with Endoplasmic Reticulum and Golgi Processing α1,2-mannosidases", *Glycobiology*, vol. 8, No. 10, pp. 981-995 (1998).

Tremblay, L.O., et al., "Cloning and Expression of a Specific Human α1,2-mannosidase that Trims $Man_9GlcNAc_2$ to $Man_8GlcNAc_2$ Isomer B During *N*-glycan Biosynthesis", *Glycobiology*, vol. 9, No. 10, pp. 1073-1078 (1999).

Gonzalez, D.S., et al., "Identification, Expression, and Characterization of a cDNA Encoding Human Endoplasmic Reticulum Mannosidase I, the Enzyme That Catalyzes the First Mannose Trimming Step in Mammalian Asn-linked Oligosaccharide Biosynthesis", *The Journal of Biological Chemistry*, vol. 274, No. 30, pp. 21375-21386 (1999).

Kniskern, P.J., et al., "Characterization and Evaluation of a Recombinant Hepatitis B Vaccine Expressed in Yeast Defective for N-linked Hyperglycoslation", *Vaccine*, vol. 11, No. 12, pp. 1021-1025 (1994).

Nakayama, K., et al., "*OCH*1 Encodes a Novel Membrane Bound Mannosyltransferase: Outer Chain Elongation of Asparagines-linked Oligosaccharides", *The EMBO Journal*, vol. 11, No. 7, pp. 2511-2519 (1992).

Callewaert, N., et al., "Use of HDEL-Tagged *Trichoderm reesei* Mannosyl Oligosaccharide 1,2-α-D-Mannosidase for N-Glycan Engineering in *Pichia pastoris*", *FEBS Letters*, vol. 503, No. 2-3, pp. 173-178 (2001).

Chen, X., et al., "Carbohydrates in Transplantation", *Current Opinion in Chemical Biology*, pp. 650-658 (1999).

Choi, B.K., et al., "Use of Combinatorial Genetic Libraries to Humanize N-linked Glycosylation in the Yeast *Pichia pastoris*", *Proceedings of the National Academy of Sciences of the United States*, vol. 100, No. 9, pp. 5022-5027 (2003).

Hamilton, S.R., et al., "Production of Complex Human Glycoproteins in Yeast", *Science*, vol. 301, No. 5637, pp. 1244-1246 (2003).

Routier F. H. et al., "The glycosylation pattern of a humanized IgGI antibody (D1.3) expressed in CHO cells", *Glycoconjugate Journal* 14: 201-207 (1997).

Kornfeld R. et al., "Assembly Of Asparagine-Linked Oligosaccharides", *Ann. Rev. Biochem. 54*: 631-664 (1985).

Malissard M. et al., "Expression of Functional Soluble Forms of Human β-1,4-Galactosyltransferase 1, α-2,6-Siayltransferase, and α-1,3-Fucosyltransferase VI in the Methylotrophic Yeast *Pichia pastoris*", *Biochemical and Biophysical Research Communications 267*: 169-173 (2000).

Bencurova M. et al., "Expression of eukaryotic glycosyltransferases in the yeast *Pichia pastoris*", *Biochimie 85*: 413-422 (2003).

Schwientek T. et al., "Golgi Localization and in Vivo Activity of a Mammalian Glycosyltransferase (Human β1, 4-Galactosyltransferase) in Yeast", *The Journal of Biological Chemistry 271*(7): 3398-3405 (1996).

Vervecken W. et al., "In Vivo Synthesis of Mammalian-Like, Hybrid-Type N-Glycans in *Pichia pastoris*", *Applied and Environmental Microbiology 70*(5): 2639-2646 (2004).

Bobrowicz P. et al., "Engineering of an artificial glycosylation pathway blocked in core oligosaccharide assembly in the yeast *Pichia pastoris*: production of complex humanized glycoproteins with terminal galactose", *Glycobiology 14*(9): 757-766 (2004).

Czlapinski J. L. et al., "Synthetic glycobiology: exploits in the Golgi compartment", *Current Opinion in Chemical Biology 10*: 645-651 (2006).

\* cited by examiner

```
                        SEQUENCE LISTING

<160> NUMBER OF SEQ ID NOS: 21

<210> SEQ ID NO 1
<211> LENGTH: 4
<212> TYPE: PRT
<213> ORGANISM: Artificial Sequence
<220> FEATURE:
<223> OTHER INFORMATION: ER-localization signal

<400> SEQUENCE: 1

His Asp Glu Leu
1

<210> SEQ ID NO 2
<211> LENGTH: 2858
<212> TYPE: DNA
<213> ORGANISM: Pichia Pastoris

<400> SEQUENCE: 2
agatctgcct gacagcctta aagagcccgc taaaagaccc ggaaaaccga gagaactctg      60
gattagcagt ctgaaaaaga atcttcactc tgtctagtgg agcaattaat gtcttagcgg     120
cacttcctgc tactccgcca gctactcctg aatagatcac atactgcaaa gactgcttgt     180
cgatgacctt ggggttattt agcttcaagg gcaattttg ggacattttg gacacaggag      240
actcagaaac agacacagag cgttctgagt cctggtgctc ctgacgtagg cctagaacag     300
gaattattgg ctttatttgt ttgtccattt cataggcttg gggtaataga tagatgacag     360
agaaatagag aagacctaat attttttgtt catggcaaat cgcgggttcg cggtcgggtc     420
acacacggag aagtaatgag aagagctggt aatctggggt aaaagggttc aaaagaaggt     480
cgcctggtag ggatgcaata caaggttgtc ttggagttta cattgaccag atgatttggc     540
tttttctctg ttcaattcac atttttcagc gagaatcgga ttgacggaga aatggcgggg    600
tgtggggtgg atagatggca gaaatgctcg caataccgc gaaagaaaga ctttatggaa     660
tagaactact gggtggtgta aggattacat agctagtcca atggagtccg ttggaaaggt     720
aagaagaagc taaaaccggc taagtaacta gggaagaatg atcagacttt gatttgatga     780
ggtctgaaaa tactctgctg cttttttcagt tgctttttcc ctgcaaccta tcatttcct    840 tttcataagc ctgccttttc tgttttcact tatatgagtt ccgccgagac ttccccaaat     900
tctctcctgg aacattctct atcgctctcc ttccaagttg cgcccctgg cactgcctag     960 taatattacc acgcgactta tattcagttc cacaatttcc agtgttcgta gcaaatatca    1020
tcagccatgg cgaaggcaga tggcagtttg ctctactata atcctcacaa tccacccaga    1080
aggtattact tctacatggc tatattcgcc gtttctgtca tttgcgtttt gtacggaccc    1140
tcacaacaat tatcatctcc aaaaatagac tatgatccat tgacgctccg atcacttgat    1200
ttgaagactt tggaagctcc ttcacagttg agtccaggca ccgtagaaga taatcttcga    1260
agacaattgg agtttcattt tccttaccgc agttacgaac cttttcccca acatatttgg    1320
caaacgtgga aagtttctcc ctctgatagt tcctttccga aaaacttcaa agacttaggt    1380
gaaagttggc tgcaaaggtc cccaaattat gatcattttg tgatacccga tgatgcagca    1440
```

-continued

```
tgggaactta ttcaccatga atacgaacgt gtaccagaag tcttggaagc tttccacctg    1500
ctaccagagc ccattctaaa ggccgatttt ttcaggtatt tgattctttt tgcccgtgga    1560
ggactgtatg ctgacatgga cactatgtta ttaaaaccaa tagaatcgtg gctgactttc    1620
aatgaaacta ttggtggagt aaaaaacaat gctgggttgg tcattggtat tgaggctgat    1680
cctgatagac ctgattggca cgactggtat gctagaagga tacaattttg ccaatgggca    1740
attcagtcca aacgaggaca cccagcactg cgtgaactga ttgtaagagt tgtcagcacg    1800
actttacgga aagagaaaag cggttacttg aacatggtgg aaggaaagga tcgtggaagt    1860
gatgtgatgg actggacggg tccaggaata tttacagaca ctctatttga ttatatgact    1920
aatgtcaata caacaggcca ctcaggccaa ggaattggag ctggctcagc gtattacaat    1980
gccttatcgt tggaagaacg tgatgccctc tctgcccgcc cgaacggaga gatgttaaaa    2040
gagaaagtcc caggtaaata tgcacagcag gttgttttat gggaacaatt taccaacctg    2100
cgctccccca aattaatcga cgatattctt attcttccga tcaccagctt cagtccaggg    2160
attggccaca gtggagctgg agatttgaac catcaccttg catatattag gcatacattt    2220
gaaggaagtt ggaaggacta agaaagcta gagtaaaata gatatagcga gattagagaa    2280
tgaatacctt cttctaagcg atcgtccgtc atcatagaat atcatggact gtatagtttt    2340
ttttttgtac atataatgat taaacggtca tccaacatct cgttgacaga tctctcagta    2400
cgcgaaatcc ctgactatca aagcaagaac cgatgaagaa aaaaacaaca gtaacccaaa    2460
caccacaaca aacactttat cttctccccc ccaacaccaa tcatcaaaga gatgtcggaa    2520
cacaaacacc aagaagcaaa aactaaccccc atataaaaac atcctggtag ataatgctgg    2580
taacccgctc tccttccata ttctgggcta cttcacgaag tctgaccggt tcagttgat    2640 caacatgatc ctcgaaatgg gtggcaagca tcgttccaga cctgcctcct ctggtagatg    2700
gagtgttgtt tttgacaggg gattacaagt ctattgatga agatacccta aagcaactgg    2760
gggacgttcc aatatacaga gactccttca tctaccagtg ttttgtgcac aagacatctc    2820
ttcccattga cactttccga attgacaaga acgtcgac                            2858
```

<210> SEQ ID NO 3
<211> LENGTH: 404
<212> TYPE: PRT
<213> ORGANISM: Pichia Pastoris

<400> SEQUENCE: 3

```
Met Ala Lys Ala Asp Gly Ser Leu Leu Tyr Tyr Asn Pro His Asn Pro
1               5                  10                   15

Pro Arg Arg Tyr Tyr Phe Tyr Met Ala Ile Phe Ala Val Ser Val Ile
            20                  25                   30

Cys Val Leu Tyr Gly Pro Ser Gln Gln Leu Ser Ser Pro Lys Ile Asp
        35                  40                   45

Tyr Asp Pro Leu Thr Leu Arg Ser Leu Asp Leu Lys Thr Leu Glu Ala
    50                  55                   60

Pro Ser Gln Leu Ser Pro Gly Thr Val Glu Asp Asn Leu Arg Arg Gln
65                  70                   75                   80

Leu Glu Phe His Phe Pro Tyr Arg Ser Tyr Glu Pro Phe Pro Gln His
                85                   90                   95

Ile Trp Gln Thr Trp Lys Val Ser Pro Ser Asp Ser Ser Phe Pro Lys
            100                 105                  110

Asn Phe Lys Asp Leu Gly Glu Ser Trp Leu Gln Arg Ser Pro Asn Tyr
```

-continued

```
            115                 120                 125
Asp His Phe Val Ile Pro Asp Ala Ala Trp Glu Leu Ile His His
    130                 135                 140
Glu Tyr Glu Arg Val Pro Glu Val Leu Glu Ala Phe His Leu Leu Pro
145                 150                 155                 160
Glu Pro Ile Leu Lys Ala Asp Phe Phe Arg Tyr Leu Ile Leu Phe Ala
            165                 170                 175
Arg Gly Gly Leu Tyr Ala Asp Met Asp Thr Met Leu Leu Lys Pro Ile
            180                 185                 190
Glu Ser Trp Leu Thr Phe Asn Glu Thr Ile Gly Gly Val Lys Asn Asn
            195                 200                 205
Ala Gly Leu Val Ile Gly Ile Glu Ala Asp Pro Asp Arg Pro Asp Trp
    210                 215                 220
His Asp Trp Tyr Ala Arg Arg Ile Gln Phe Cys Gln Trp Ala Ile Gln
225                 230                 235                 240
Ser Lys Arg Gly His Pro Ala Leu Arg Glu Leu Ile Val Arg Val Val
            245                 250                 255
Ser Thr Thr Leu Arg Lys Glu Lys Ser Gly Tyr Leu Asn Met Val Glu
            260                 265                 270
Gly Lys Asp Arg Gly Ser Asp Val Met Asp Trp Thr Gly Pro Gly Ile
            275                 280                 285
Phe Thr Asp Thr Leu Phe Asp Tyr Met Thr Asn Val Asn Thr Thr Gly
    290                 295                 300
His Ser Gly Gln Gly Ile Gly Ala Gly Ser Ala Tyr Tyr Asn Ala Leu
305                 310                 315                 320
Ser Leu Glu Glu Arg Asp Ala Leu Ser Ala Arg Pro Asn Gly Glu Met
            325                 330                 335
Leu Lys Glu Lys Val Pro Gly Lys Tyr Ala Gln Gln Val Val Leu Trp
            340                 345                 350
Glu Gln Phe Thr Asn Leu Arg Ser Pro Lys Leu Ile Asp Asp Ile Leu
            355                 360                 365
Ile Leu Pro Ile Thr Ser Phe Ser Pro Gly Ile Gly His Ser Gly Ala
    370                 375                 380
Gly Asp Leu Asn His His Leu Ala Tyr Ile Arg His Thr Phe Glu Gly
385                 390                 395                 400
Ser Trp Lys Asp
```

<210> SEQ ID NO 4
<211> LENGTH: 43
<212> TYPE: DNA
<213> ORGANISM: Artificial Sequence
<220> FEATURE:
<223> OTHER INFORMATION: Oligonucleotide primer

<400> SEQUENCE: 4
ggaattcagc atggagtatg gatcatggag tccgttggaa agg         43

<210> SEQ ID NO 5
<211> LENGTH: 27
<212> TYPE: DNA
<213> ORGANISM: Artificial Sequence
<220> FEATURE:
<223> OTHER INFORMATION: Oligonucleotide primer

<400> SEQUENCE: 5
gccgctcgag ctagctttct ttagtcc         27

<210> SEQ ID NO 6
<211> LENGTH: 2875
<212> TYPE: DNA
<213> ORGANISM: Artificial Sequence
<220> FEATURE:
<223> OTHER INFORMATION: Nucleotide Sequence of plasmid pGlycoSwitchM8

<400> SEQUENCE: 6

| | | | | | |
|---|---|---|---|---|---|
| agatctaaca | tccataatcg | atctaagcta | tattcgccgt | ttctgtcatt | tgcgttttgt | 60 |
| acggaccctc | acaacaatta | tcatctccaa | aaatagacta | tgatccattg | acgctccgat | 120 |
| cacttgattt | gaagactttg | gaagctcctt | cacagttgag | tccaggcacc | gtagaagata | 180 |
| atcttcgaag | acaattggag | tttcattttc | cttaccgcag | ttacgaacct | tttccccaac | 240 |
| atatttggca | aacgtggaaa | gtttctccct | ctgatagttc | ctttccgaaa | aacttcaaag | 300 |
| acttaggtga | aagttggctg | caaaggtccc | caaattatga | tcattttgtg | tacccgatg | 360 |
| atgcagcatg | gaacttatt | caccatgaat | acgaacgtgt | accagaagtc | ttggaagctt | 420 |
| ttgattttaa | cgacttttaa | cgacaacttg | agaagatcaa | aaaacaacta | attattcgcg | 480 |
| aaacgaggaa | ttcacgtggc | ccagccggcc | gtctcggatc | ggtacctcga | gccgcggcgg | 540 |
| ccgccagctt | tctagagaac | aaaaactcat | ctcagaagag | gatctgaata | gcgccgtcga | 600 |
| ccatcatcat | catcatcatt | gagtttgtag | ccttagacat | gactgttcct | cagttcaagt | 660 |
| tgggcactta | cgagaagacc | ggtcttgcta | gattctaatc | aagaggatgt | cagaatgcca | 720 |
| tttgcctgag | agatgcaggc | ttcatttttg | atacttttt | atttgtaacc | tatatagtat | 780 |
| aggattttt | ttgtcatttt | gtttcttctc | gtacgagctt | gctcctgatc | agcctatctc | 840 |
| gcagctgatg | aatatcttgt | ggtaggggtt | tgggaaaatc | attcgagttt | gatgttttc | 900 |
| ttggtatttc | ccactcctct | tcagagtaca | gaagattaag | tgagaccttc | gtttgtgcgg | 960 |
| atcccccaca | caccatagct | tcaaaatgtt | tctactcctt | ttttactctt | ccagattttc | 1020 |
| tcggactccg | cgcatcgccg | taccacttca | aaacacccaa | gcacagcata | ctaaattttc | 1080 |
| cctctttctt | cctctagggt | gtcgttaatt | acccgtacta | aagtttgga | aagaaaaaa | 1140 |
| gagaccgcct | cgtttctttt | tcttcgtcga | aaaaggcaat | aaaaatttt | atcacgtttc | 1200 |
| tttttcttga | atttttttt | tttagttttt | ttctctttca | gtgacctcca | ttgatattta | 1260 |
| agttaataaa | cggtcttcaa | tttctcaagt | ttcagtttca | tttttcttgt | tctattacaa | 1320 |
| ctttttttac | ttcttgttca | ttagaaagaa | agcatagcaa | tctaatctaa | ggggcggtgt | 1380 |
| tgacaattaa | tcatcggcat | agtatatcgg | catagtataa | tacgacaagg | tgaggaacta | 1440 |
| aaccatggcc | aagttgacca | gtgccgttcc | ggtgctcacc | gcgcgcgacg | tcgccggagc | 1500 |
| ggtcgagttc | tggaccgacc | ggctcgggtt | ctcccgggac | ttcgtggagg | acgacttcgc | 1560 |
| cggtgtggtc | cgggacgacg | tgaccctgtt | catcagcgcg | gtccaggacc | aggtggtgcc | 1620 |
| ggacaacacc | ctggcctggg | tgtgggtgcg | cggcctggac | gagctgtacg | ccgagtggtc | 1680 |
| ggaggtcgtg | tccacgaact | tccgggacgc | ctccgggccg | gccatgaccg | agatcggcga | 1740 |
| gcagccgtgg | gggcgggagt | tcgccctgcg | cgacccggcc | ggcaactgcg | tgcacttcgt | 1800 |
| ggccgaggag | caggactgac | acgtccgacg | gcggcccacg | ggtcccaggc | ctcggagatc | 1860 |
| cgtccccctt | ttcctttgtc | gatatcatgt | aattagttat | gtcacgctta | cattcacgcc | 1920 |
| ctccccccac | atccgctcta | accgaaaagg | aaggagttag | acaacctgaa | gtctaggtcc | 1980 |
| ctatttattt | tttatagtt | atgttagtat | taagaacgtt | atttatattt | caaatttttc | 2040 |
| ttttttttct | gtacagacgc | gtgtacgcat | gtaacattat | actgaaaacc | ttgcttgaga | 2100 |

-continued

```
aggttttggg acgctcgaag gctttaattt gcaagctgga gaccaacatg tgagcaaaag    2160
gccagcaaaa ggccaggaac cgtaaaaagg ccgcgttgct ggcgtttttc cataggctcc    2220 gccccctga cgagcatcac aaaaatcgac gctcaagtca gaggtggcga acccgacag     2280 gactataaag ataccaggcg tttccccctg gaagctccct cgtgcgctct cctgttccga    2340
ccctgccgct taccggatac ctgtccgcct ttctcccttc gggaagcgtg gcgctttctc    2400
aatgctcacg ctgtaggtat ctcagttcgg tgtaggtcgt tcgctccaag ctgggctgtg    2460
tgcacgaacc ccccgttcag cccgaccgct gcgccttatc cggtaactat cgtcttgagt    2520
ccaacccggt aagacacgac ttatcgccac tggcagcagc cactggtaac aggattagca    2580
gagcgaggta tgtaggcggt gctacagagt tcttgaagtg gtggcctaac tacggctaca    2640
ctagaaggac agtatttggt atctgcgctc tgctgaagcc agttaccttc ggaaaaagag    2700
ttggtagctc ttgatccggc aaacaaacca ccgctggtag cggtggtttt tttgtttgca    2760
agcagcagat tacgcgcaga aaaaaggat ctcaagaaga tcctttgatc ttttctacgg     2820
ggtctgacgc tcagtggaac gaaaactcac gttaagggat tttggtcatg agatc         2875
```

<210> SEQ ID NO 7
<211> LENGTH: 6406
<212> TYPE: DNA
<213> ORGANISM: Artificial Sequence
<220> FEATURE:
<223> OTHER INFORMATION: Nucleotide sequence of plasmid
      pB1KanMX4KrehGalT

<400> SEQUENCE: 7

```
ctagtgcaca acgaacgtc tcacttaatc ttctgtactc tgaagaggag tgggaaatac      60
caagaaaaac atcaaactcg aatgattttc ccaaacccct accacaagat attcatcagc    120
tgcgagatag gctgatcagg agcaagctcg tacgagaaga aacaaaatga caaaaaaat    180 cctatactat ataggttaca aataaaaaag tatcaaaaat gaagcctgca tctctcaggc    240
aaatggcatt ctgacatcct cttgattaga atctagcaag accggtcttc tcgtaagtgc    300
ccaacttgaa ctgaggaaca gtcatgtcta aggcgaatta tcaagcttag ctcggtgtcc    360
cgatgtccac tgtgatttgg gtatacaatg ggtatctctg tacatccagc acctggtagg    420
tgagtgagtt caaaccatca gagagcattg tctcctttgt gtgtgcaatt cggtcaaacc    480
tctgaggatt gggttcattt ttttgtctc ttgagtggcg gatcatgcga cacctcccga    540
ccacagcatt tgggcgagat atagacatgc ctctaaaaac taatctgtta aaaatgtcat    600
catcttctcc tccccagccc caataattat taggaaatcc attgatggtt agaaactgtt    660
gtttacttag agcagagaca cctccaaaat actgaacata aggtaggctg aatccaaact    720
tatccattgc aacggaaatg tgccgtggct gtgaaaaaca cctgtacgca ttatggtcat    780
tcattggaat gaggtccacg tcactaaaca caaagcaggt gtagtcatag tccttcaagg    840
cttcttgaaa gccaacattg aggagcttag cacgattgaa tatagtgtct cccgcctggt    900
tgataacata gatgccatag tccagctgct ggcgctgcag gactgggtgc aaataatata    960
gccagtactt gaggtgctcc tgccggttgc ggaatggaat gatgatggcc accttgtgag   1020
gagagacgca gtccctgggg gcatagcggc cgcccatctt cacatttggg ttctgctttg   1080
ccacgagctc caggtccaca ggcatgttaa actcaatcag catggggccc acaagcagcg   1140
gggactcctc agggcaggcg ggcagcgaca gtgcggtggt gtgggcact gggaccgagg    1200 tcaagttgct agcggggcca gggccagaat ccacgactgg gctggagtcg ccacccgggc   1260
```

```
gcggctggga ggaggcgcct agaggaggcg gcggccgggc ccctccggtc gccggcgggg    1320
catctgcctt ttcagcggca gctttcagag ccttggattc ttcatccatg gcttcggagt    1380
cttcgcttgc ctctgaattc agagcacttt gctctaattt tttagcatca ttttcctcag    1440
agatgacttg ttgttcaggg gatatagatc ctgaggtaaa atcaaatgca gcggagatgg    1500
aactcggaat atattgctga gttctactgt tggaattcaa tgttaggagg agaacaataa    1560
ccgcacctgc aatgacggta aatctcaaca gtctcttact gagaaagagg gccatcttaa    1620
gttcgaataa ttagttgttt tttgatcttc tcaagttgtc gttaaaagtc gttaaaatca    1680
aaagcttgtc aattggaacc agtcgcaatt atgaaagtaa gctaataatg atgataaaaa    1740
aaaaggttta agacagggca gcttccttct gtttatatat tgctgtcaag taggggttag    1800
aacagttaaa ttttgatcat gaacgttagg ctatcagcag tattcccacc agaatcttgg    1860
aagcatacaa tgtggagaca atgcataatc atccaaaaag cgggtgtttc cccatttgcg    1920
tttcggcaca ggtgcaccgg ggttcagaag cgatagagag actgcgctaa gcattaatga    1980
gattattttt gagcattcgt caatcaatac caaacaagac aaacggtatg ccgacttttg    2040
gaagtttctt tttgaccaac tggccgttag catttcaacg aaccaaactt agttcatctt    2100
ggatgagatc acgcttttgt catattaggt tccaagacag cgtttaaact gtcagttttg    2160
ggccatttgg ggaacatgaa actatttgac cccacactca gaaagccctc atctggagtg    2220
atgttcgggt gtaatgcgga gcttgttgca ttcggaaata aacaaacatg aacctcgcca    2280 gggggggccag gatagacagg ctaataaagt catggtgtta gtagcctaat agaaggaatt    2340
ggaatgagcg agctccaatc aagcccaata actgggctgg ttttttcgatg gcaaaagtgg    2400 gtgttgagga agagagagt ggaggtcctg cgtttgcaac ggtctgctgc tagtgtatcc    2460
cctcctgttg cgtttggcac ttatgtgtga gaatggacct gtggatgtcg gatggcaaaa    2520
aggtttcatt caacctttcg tctttggatg ttagctagcc ggctgcatta atgaatcggc    2580
caacgcgcgg ggagaggcgg tttgcgtatt gggcgctctt ccgcttcctc gctcactgac    2640
tcgctgcgct cggtcgttcg gctgcggcga gcggtatcag ctcactcaaa ggcggtaata    2700
cggttatcca cagaatcagg ggataacgca ggaaagaaca tgtgagcaaa aggccagcaa    2760
aaggccagga accgtaaaaa ggccgcgttg ctggcgtttt tccataggct ccgcccccct    2820
gacgagcatc acaaaaatcg acgctcaagt cagaggtggc gaaacccgac aggactataa    2880
agataccagg cgtttccccc tggaagctcc ctcgtgcgct ctcctgttcc gaccctgccg    2940
cttaccggat acctgtccgc ctttctccct tcgggaagcg tggcgctttc tcatagctca    3000
cgctgtaggt atctcagttc ggtgtaggtc gttcgctcca agctgggctg tgtgcacgaa    3060
ccccccgttc agcccgaccg ctgcgcctta tccggtaact atcgtcttga gtccaacccg    3120
gtaagacacg acttatcgcc actggcagca gccactggta acaggattag cagagcgagg    3180
tatgtaggcg gtgctacaga gttcttgaag tggtggccta actacggcta cactagaagg    3240
acagtatttg gtatctgcgc tctgctgaag ccagttacct tcggaaaaag agttggtagc    3300
tcttgatccg gcaaacaaac caccgctggt agcggtggtt tttttgtttg caagcagcag    3360
attacgcgca gaaaaaaagg atctcaagaa gatcctttga tcttttctac ggggtctgac    3420
gctcagtgga acgaaaactc acgttaaggg attttggtca tgagattatc aaaaaggatc    3480
ttcacctaga tccttttaaa ttaaaaatga agttttaaat caatctaaag tatatatgag    3540
taaacttggt ctgacagtta ccaatgctta atcagtgagg cacctatctc agcgatctgt    3600
```

-continued

```
ctatttcgtt catccatagt tgcctgactc cccgtcgtgt agataactac gatacgggag   3660
ggcttaccat ctggccccag tgctgcaatg ataccgcgag acccacgctc accggctcca   3720
gatttatcag caataaacca gccagccgga agggccgagc gcagaagtgg tcctgcaact   3780
ttatccgcct ccatccagtc tattaattgt tgccgggaag ctagagtaag tagttcgcca   3840
gttaatagtt tgcgcaacgt tgttgccatt gctacaggca tcgtggtgtc acgctcgtcg   3900
tttggtatgg cttcattcag ctccggttcc caacgatcaa ggcgagttac atgatccccc   3960
atgttgtgca aaaagcggt tagctccttc ggtcctccga tcgttgtcag aagtaagttg   4020
gccgcagtgt tatcactcat ggttatggca gcactgcata attctcttac tgtcatgcca   4080
tccgtaagat gcttttctgt gactggtgag tactcaacca agtcattctg agaatagtgt   4140
atgcggcgac cgagttgctc ttgcccggcg tcaatacggg ataataccgc gccacatagc   4200
agaactttaa aagtgctcat cattggaaaa cgttcttcgg ggcgaaaact ctcaaggatc   4260
ttaccgctgt tgagatccag ttcgatgtaa cccactcgtg cacccaactg atcttcagca   4320
tcttttactt tcaccagcgt ttctgggtga gcaaaaacag gaaggcaaaa tgccgcaaaa   4380
aagggaataa gggcgacacg gaaatgttga atactcatac tcttcctttt tcaatgcttc   4440
tagtggtagg aattaattct gtaccggttt acagaaggac gactcttgat gcgccaacca   4500
cagtgacaat agacatagag gaaatgcaaa aaggattatg cgaggatgct gctggagacg   4560
attcaaagtt tagtttagaa aggtcctcca tttatgctga tagaatacta gatacccgtg   4620
aactttgtct caggagatcc gcatcagacg aaggatgttc cgacctgcaa ataatcgaag   4680
aagagacccc taggcagttg gtgagcttac atgagaagtc taaactatct tggacccgct   4740
ggttttataa agggttcgtt aggaatgcgt taactaccat tccagcaaca tccgtggggc   4800
ttctggtgtt tgaaatactg cgtcaaaaat tgagcgatga aattgaagat cgattcagtt   4860
gaatcgcccg aaacaattga tcccctgtac atacttgtaa tttacctcag aatgggttaa   4920
ttaaggcgcg ccagatctgt ttagcttgcc tcgtccccgc cgggtcaccc ggccagcgac   4980
atggaggccc agaataccct ccttgacagt cttgacgtgc gcagctcagg gcatgatgt    5040 gactgtcgcc cgtacattta gcccatacat ccccatgtat aatcatttgc atccatacat   5100
tttgatggcc gcacggcgcg aagcaaaaat tacggctcct cgctgcagac ctgcgagcag   5160
ggaaacgctc ccctcacaga cgcgttgaat tgtccccacg ccgcgcccct gtagagaaat   5220
ataaaaggtt aggatttgcc actgaggttc ttctttcata tacttccttt taaaatcttg   5280
ctaggataca gttctcacat cacatccgaa cataaacaac catgggtaag gaaaagactc   5340
acgtttcgag gccgcgatta aattccaaca tggatgctga tttatatggg tataaatggg   5400
ctcgcgataa tgtcgggcaa tcaggtgcga caatctatcg attgtatggg aagcccgatg   5460
cgccagagtt gtttctgaaa catggcaaag gtagcgttgc caatgatgtt acagatgaga   5520
tggtcagact aaactggctg acggaattta tgcctcttcc gaccatcaag cattttatcc   5580
gtactcctga tgatgcatgg ttactcacca ctgcgatccc cggcaaaaca gcattccagg   5640
tattagaaga atatcctgat tcaggtgaaa atattgttga tgcgctggca gtgttcctgc   5700
gccggttgca ttcgattcct gtttgtaatt gtccttttaa cagcgatcgc gtatttcgtc   5760
tcgctcaggc gcaatcacga tgaataacg gtttggttga tgcgagtgat tttgatgacg   5820
agcgtaatgg ctggcctgtt gaacaagtct ggaaagaaat gcataagctt ttgccattct   5880
caccggattc agtcgtcact catggtgatt tctcacttga taaccttatt tttgacgagg   5940
ggaaattaat aggttgtatt gatgttggac gagtcggaat cgcagaccga taccaggatc   6000
```

```
ttgccatcct atgaactgc ctcggtgagt tttctccttc attacagaaa cggcttttc      6060 aaaaatatgg tattgataat cctgatatga ataaattgca gtttcatttg atgctcgatg      6120
agttttctta atcagtactg acaataaaaa gattcttgtt ttcaagaact tgtcatttgt      6180 atagttttt tatattgtag ttgttctatt ttaatcaaat gttagcgtga tttatatttt       6240
ttttcgcctc gacatcatct gcccagatgc gaagttaagt gcgcagaaag taatatcatg      6300
cgtcaatcgt atgtgaatgc tggtcgctat actgctgtcg attcgatact aacgccgcca      6360
tccagtgtcg aaaacgagct cgaattcatc gatgatatca gatcca                    6406
```

<210> SEQ ID NO 8
<211> LENGTH: 1785
<212> TYPE: DNA
<213> ORGANISM: Artificial Sequence
<220> FEATURE:
<223> OTHER INFORMATION: ORF sequence of MFManHDEL fusion in
      pGAPZMFManHDEL

<400> SEQUENCE: 8

```
atgagatttc cttcaatttt tactgctgtt ttattcgcag catcctccgc attagctgct        60
ccagtcaaca ctacaacaga agatgaaacg gcacaaattc cggctgaagc tgtcatcggt       120
tactcagatt tagaagggga tttcgatgtt gctgttttgc catttccaa cagcacaaat        180 aacgggttat tgtttataaa tactactatt gccagcattg ctgctaaaga agaaggggta       240
tctctcgaga aaagagaggc tgaagctgaa ttcgccacaa acgtggatc tcccaaccct        300 acgagggcgg cagcagtcaa ggccgcattc agacgtcgt ggaacgctta ccaccatttt       360
gccttccccc atgacgacct ccacccggtc agcaacagc ttgatgatga gagaaacggc       420
tggggctcgt cggcaatcga tggcttggac acggctatcc tcatgggga tgccgacatt       480 gtgaacacga tccttcagta tgtaccgcag atcaacttca ccacgactgc ggttgccaac      540
caaggatcct ccgtgttcga gaccaacatt cggtacctcg gtggcctgct ttctgcctat     600
gacctgttgc gaggtccttt cagctccttg gcgacaaacc agaccctggt aaacagcctt      660
ctgaggcagg ctcaaacact ggccaacggc tcaaggttg cgttcaccac tcccagcggt       720
gtcccggacc ctaccgtctt cttcaaccct actgtccgga aagtggtgc atctagcaac       780 aacgtcgctg aaattggaag cctggtgctc gagtggacac ggttgagcga cctgacggga      840
aacccgcagt atgcccagct tgcgcagaag ggcgagtcgt atctcctgaa tccaaaggga      900
agcccggagg catggcctgg cctgattgga acgtttgtca gcacgagcaa cggtaccttt      960
caggatagca gcggcagctg gtccggcctc atggacagct tctacgagta cctgatcaag      1020
atgtacctgt acgacccggt tgcgtttgca cactacaagg atcgctgggt ccttggtgcc     1080
gactcgacca ttgggcatct cggctctcac ccgtcgacgc gcaaggactt gaccttttg      1140 tcttcgtaca cggacagtc tacgtcgcca aactcaggac atttggccag ttttggcggt      1200
ggcaacttca tcttgggagg cattctcctg aacgagcaaa agtacattga ctttggaatc      1260
aagcttgcca gctcgtactt tggcacgtac acccagacgc cttctggaat cggcccgaa       1320 ggcttcgcgt gggtggacag cgtgacgggc gccggcggct cgccgccctc gtcccagtcc      1380
gggttctact cgtcggcagg attctgggtg acggcaccgt attacatcct gcggccggag      1440
acgctggaga gcttgtacta cgcataccgc gtcacgggcg actccaagtg caggacctg       1500 gcgtgggaag cgttgagtgc cattgaggac gcatgccgcg ccggcagcgc gtactcgtcc      1560
atcaacgacg tgacgcaggc caacggcggg ggtgcctctg acgatatgga gagcttctgg      1620
```

```
tttgccgagg cgctcaagta tgcgtacctg atctttgcgg aggagtcgga tgtgcaggtg    1680
caggccaccg gcgggaacaa atttgtcttt aacacggagg cgcaccccatt tagcatccgt   1740 tcatcatcac gacggggcgg ccaccttgct cacgacgagt tgtaa                    1785

<210> SEQ ID NO 9
<211> LENGTH: 5485
<212> TYPE: DNA
<213> ORGANISM: Artificial Sequence
<220> FEATURE:
<223> OTHER INFORMATION: Nucleotide sequence of plasmid pGlycoSwitch M5

<400> SEQUENCE: 9
agatctaaca tccataatcg atctaagcta tattcgccgt ttctgtcatt tgcgttttgt      60
acggaccctc acaacaatta tcatctccaa aaatagacta tgatccattg acgctccgat    120
cacttgattt gaagactttg gaagctcctt cacagttgag tccaggcacc gtagaagata    180
atcttcgaag acaattggag tttcattttc cttaccgcag ttacgaacct tttccccaac    240
atatttggca aacgtggaaa gtttctccct ctgatagttc cttccgaaa aacttcaaag     300 acttaggtga agttggctg caaaggtccc caaattatga tcatttttgtg tacccgatg     360 atgcagcatg ggaacttatt caccatgaat acgaacgtgt accagaagtc ttggaagctc    420
tagatgctca ccgcaatgct gttaaggttc gtatggagaa actgggactt atttaattat    480
ttagagattt taacttacat ttagattcga tagatccaca ggacgggtgt ggtcgccatg    540
atcgcgtagt cgatagtggc tccaagtagc gaagcgagca ggactgggcg gcggccaaag    600
cggtcggaca gtgctccgag aacgggtgcg catagaaatt gcatcaacgc atatagcgct    660
agcagcacgc catagtgact ggcgatgctg tcggaatgga cgatatcccg caagaggccc    720
ggcagtaccg gcataaccaa gcctatgcct acagcatcca gggtgacggt gccgaggatg    780
acgatgagcg cattgttaga tttcatacac ggtgcctgac tgcgttagca atttaactgt    840
gataaactac cgcattaaag ctgatctttt ttgtagaaat gtcttggtgt cctcgtccaa    900
tcaggtagcc atctctgaaa tatctggctc cgttgcaact ccgaacgacc tgctggcaac    960
gtaaaattct ccggggtaaa acttaaatgt ggagtaatgg aaccagaaac gtctcttccc   1020
ttctctctcc ttccaccgcc cgttaccgtc cctaggaaat tttactctgc tggagagctt   1080
cttctacggc ccccttgcag caatgctctt cccagcatta cgttgcgggt aaaacggagg   1140
tcgtgtaccc gacctagcag cccagggatg gaaaagtccc ggccgtcgct ggcaataata   1200
gcgggcggac gcatgtcatg agattattgg aaaccaccag aatcgaatat aaaaggcgaa   1260 caccttttccc aattttggtt tctcctgacc caaagacttt aaatttaatt tatttgtccc   1320
tatttcaatc aattgaacaa ctatttcgcg aaacgatgag atttccttca attttttactg 1380 ctgttttatt cgcagcatcc tccgcattag ctgctccagt caacactaca acagaagatg   1440
aaacggcaca aattccggct gaagctgtca tcggttactc agatttagaa ggggatttcg   1500
atgttgctgt tttgccattt tccaacagca caaataacgg ttattgtttt ataaatacta   1560
ctattgccag cattgctgct aaagaagaag gggtatctct cgagaaaaga gaggctgaag   1620
ctgaattcgc cacaaaacgt ggatctccca accctacgag ggcggcagca gtcaaggccg   1680
cattccagac gtcgtggaac gcttaccacc atttttgcctt tccccatgac gacctccacc   1740
cggtcagcaa cagctttgat gatgagaaa acggctgggg ctcgtcggca atcgatggct   1800
tggacacggc tatcctcatg ggggatgccg acattgtgaa cacgatcctt cagtatgtac   1860
```

-continued

```
cgcagatcaa cttcaccacg actgcggttg ccaaccaagg atcctccgtg ttcgagacca   1920
acattcggta cctcggtggc ctgctttctg cctatgacct gttgcgaggt cctttcagct   1980
ccttggcgac aaaccagacc ctggtaaaca gccttctgag gcaggctcaa acactggcca   2040
acggcctcaa ggttgcgttc accactccca gcggtgtccc ggaccctacc gtcttcttca   2100
accctactgt ccggagaagt ggtgcatcta gcaacaacgt cgctgaaatt ggaagcctgg   2160
tgctcgagtg gacacggttg agcgacctga cgggaaaccc gcagtatgcc cagcttgcgc   2220
agaagggcga gtcgtatctc ctgaatccaa agggaagccc ggaggcatgg cctggcctga   2280
ttggaacgtt tgtcagcacg agcaacggta cctttcagga tagcagcggc agctggtccg   2340
gcctcatgga cagcttctac gagtacctga tcaagatgta cctgtacgac ccggttgcgt   2400
ttgcacacta caaggatcgc tgggtccttg gtgccgactc gaccattggg catctcggct   2460
ctcacccgtc gacgcgcaag gacttgacct tttgtcttc gtacaacgga cagtctacgt    2520
cgccaaactc aggacatttg gccagttttg gcggtggcaa cttcatcttg ggaggcattc   2580
tcctgaacga gcaaaagtac attgactttg gaatcaagct tgccagctcg tactttggca   2640
cgtacaccca gacggcttct ggaatcggcc ccgaaggctt cgcgtgggtg gacagcgtga   2700
cgggcgccgg cggctcgccg ccctcgtccc agtccgggtt ctactcgtcg gcaggattct   2760
gggtgacggc accgtattac atcctgcggc cggagacgct ggagagcttg tactacgcat   2820
accgcgtcac gggcgactcc aagtggcagg acctggcgtg ggaagcgttg agtgccattg   2880
aggacgcatg ccgcgccggc agcgcgtact cgtccatcaa cgacgtgacg caggccaacg   2940
gcgggggtgc ctctgacgat atggagagct tctggtttgc cgaggcgctc aagtatgcgt   3000
acctgatctt tgcggaggag tcggatgtgc aggtgcaggc caccggcggg aacaaatttg   3060
tctttaacac ggaggcgcac ccctttagca tccgttcatc atcacgacgg ggcggccacc   3120
ttgctcacga cgagttgtaa tctagggcgg ccgccagctt tctagagaac aaaaactcat   3180
ctcagaagag gatctgaata gcgccgtcga ccatcatcat catcatcatt gagtttgtag   3240
ccttagacat gactgttcct cagttcaagt tgggcactta cgagaagacc ggtcttgcta   3300
gattctaatc aagaggatgt cagaatgcca tttgcctgag agatgcaggc ttcatttttg   3360
atactttttt atttgtaacc tatatagtat aggatttttt ttgtcatttt gtttcttctc   3420
gtacgagctt gctcctgatc agcctatctc gcagctgatg aatatcttgt ggtaggggtt   3480
tgggaaaatc attcgagttt gatgtttttc ttggtatttc ccactcctct tcagagtaca   3540
gaagattaag tgagaccttc gtttgtgcgg atcccccaca caccatagct tcaaaatgtt   3600
tctactcctt ttttactctt ccagattttc tcggactccg cgcatcgccg taccacttca   3660
aaacacccaa gcacagcata ctaaatttcc cctctttctt cctctagggt gtcgttaatt   3720
acccgtacta aaggtttgga aaagaaaaaa gagaccgcct cgtttctttt tcttcgtcga   3780
aaaaggcaat aaaaattttt atcacgtttc tttttcttga aatttttttt tttagttttt   3840
ttctctttca gtgacctcca ttgatattta agttaataaa cggtcttcaa tttctcaagt   3900
ttcagtttca tttttcttgt tctattacaa cttttttttac ttcttgttca ttagaaagaa  3960
agcatagcaa tctaatctaa ggggcggtgt tgacaattaa tcatcggcat agtatatcgg   4020
catagtataa tacgacaagg tgaggaacta aaccatggcc aagttgacca gtgccgttcc   4080
ggtgctcacc gcgcgcgacg tcgccggagc ggtcgagttc tggaccgacc ggctcgggtt   4140
ctcccgggac ttcgtggagg acgacttcgc cggtgtggtc cgggacgacg tgaccctgtt   4200
catcagcgcg gtccaggacc aggtggtgcc ggacaacacc ctggcctggg tgtgggtgcg   4260
```

-continued

```
cggcctggac gagctgtacg ccgagtggtc ggaggtcgtg tccacgaact tccgggacgc    4320
ctccgggccg gccatgaccg agatcggcga gcagccgtgg gggcgggagt tcgccctgcg    4380
cgacccggcc ggcaactgcg tgcacttcgt ggccgaggag caggactgac acgtccgacg    4440
gcggcccacg ggtcccaggc ctcggagatc cgtcccccctt ttcctttgtc gatatcatgt    4500
aattagttat gtcacgctta cattcacgcc ctcccccac atccgctcta accgaaaagg     4560
aaggagttag acaacctgaa gtctaggtcc ctatttattt ttttatagtt atgttagtat    4620
taagaacgtt atttatattt caaatttttc ttttttttct gtacagacgc gtgtacgcat    4680
gtaacattat actgaaaacc ttgcttgaga aggttttggg acgctcgaag ctttaattt     4740
gcaagctgga gaccaacatg tgagcaaaag gccagcaaaa ggccaggaac cgtaaaaagg    4800
ccgcgttgct ggcgtttttc cataggctcc gcccccctga cgagcatcac aaaaatcgac    4860
gctcaagtca gaggtggcga aacccgacag gactataaag ataccaggcg tttcccctg     4920
gaagctccct cgtgcgctct cctgttccga ccctgccgct taccggatac ctgtccgcct    4980
```

<210> SEQ ID NO 10
<211> LENGTH: 441
<212> TYPE: PRT
<213> ORGANISM: S. cerevisiae

<400> SEQUENCE: 10

```
Met Ala Leu Phe Leu Ser Lys Arg Leu Leu Arg Phe Thr Val Ile Ala
1               5                   10                  15

Gly Ala Val Ile Val Leu Leu Thr Leu Asn Ser Asn Ser Arg Thr
            20                  25                  30

Gln Gln Tyr Ile Pro Ser Ser Ile Ala Ala Phe Asp Phe Thr Ser Gly
        35                  40                  45

Ser Ile Ser Pro Glu Gln Gln Val Ile Ser Glu Asn Asp Ala Lys
    50                  55                  60

Lys Leu Glu Gln Ser Ala Leu Asn Ser Glu Ala Ser Glu Asp Ser Glu
65                  70                  75                  80

Ala Met Asp Glu Glu Ser Lys Ala Leu Lys Ala Ala Glu Lys Ala
                85                  90                  95

Asp Ala Pro Ile Asp Thr Lys Thr Thr Met Asp Tyr Ile Thr Pro Ser
            100                 105                 110

Phe Ala Asn Lys Ala Gly Lys Pro Lys Ala Cys Tyr Val Thr Leu Val
        115                 120                 125

Arg Asn Lys Glu Leu Lys Gly Leu Leu Ser Ser Ile Lys Tyr Val Glu
    130                 135                 140

Asn Lys Ile Asn Lys Lys Phe Pro Tyr Pro Trp Val Phe Leu Asn Asp
```

```
                145                 150                 155                 160
Glu Pro Phe Thr Glu Glu Phe Lys Glu Ala Val Thr Lys Ala Val Ser
                    165                 170                 175

Ser Glu Val Lys Phe Gly Ile Leu Pro Lys Glu His Trp Ser Tyr Pro
                    180                 185                 190

Glu Trp Ile Asn Gln Thr Lys Ala Ala Glu Ile Arg Ala Asp Ala Ala
                    195                 200                 205

Thr Lys Tyr Ile Tyr Gly Gly Ser Glu Ser Tyr Arg His Met Cys Arg
                    210                 215                 220

Tyr Gln Ser Gly Phe Phe Trp Arg His Glu Leu Leu Glu Tyr Asp
225                 230                 235                 240

Trp Tyr Trp Arg Val Glu Pro Asp Ile Lys Leu Tyr Cys Asp Ile Asn
                    245                 250                 255

Tyr Asp Val Phe Lys Trp Met Gln Glu Asn Glu Lys Val Tyr Gly Phe
                    260                 265                 270

Thr Val Ser Ile His Glu Tyr Glu Val Thr Ile Pro Thr Leu Trp Gln
                    275                 280                 285

Thr Ser Met Asp Phe Ile Lys Lys Asn Pro Glu Tyr Leu Asp Glu Asn
                    290                 295                 300

Asn Leu Met Ser Phe Leu Ser Asn Asp Asn Gly Lys Thr Tyr Asn Leu
305                 310                 315                 320

Cys His Phe Trp Ser Asn Phe Glu Ile Ala Asn Leu Asn Leu Trp Arg
                    325                 330                 335

Ser Pro Ala Tyr Arg Glu Tyr Phe Asp Thr Leu Asp His Gln Gly Gly
                    340                 345                 350

Phe Phe Tyr Glu Arg Trp Gly Asp Ala Pro Val His Ser Ile Ala Ala
                    355                 360                 365

Ala Leu Phe Leu Pro Lys Asp Lys Ile His Tyr Phe Ser Asp Ile Gly
                    370                 375                 380

Tyr His His Pro Pro Tyr Asp Asn Cys Pro Leu Asp Lys Glu Val Tyr
385                 390                 395                 400

Asn Ser Asn Asn Cys Glu Cys Asp Gln Gly Asn Asp Phe Thr Phe Gln
                    405                 410                 415

Gly Tyr Ser Cys Gly Lys Glu Tyr Tyr Asp Ala Gln Gly Leu Val Lys
                    420                 425                 430

Pro Lys Asn Trp Lys Lys Phe Arg Glu
                    435                 440

<210> SEQ ID NO 11
<211> LENGTH: 100
<212> TYPE: PRT
<213> ORGANISM: S. cerevisiae

<400> SEQUENCE: 11

Met Ala Leu Phe Leu Ser Lys Arg Leu Leu Arg Phe Thr Val Ile Ala
1               5                   10                  15

Gly Ala Val Ile Val Leu Leu Thr Leu Asn Ser Asn Ser Arg Thr
                20                  25                  30

Gln Gln Tyr Ile Pro Ser Ser Ile Ser Ala Ala Phe Asp Phe Thr Ser
                35                  40                  45

Gly Ser Ile Ser Pro Glu Gln Gln Val Ile Ser Glu Glu Asn Asp Ala
            50                  55                  60

Lys Lys Leu Glu Gln Ser Ala Leu Asn Ser Glu Ala Ser Glu Asp Ser
65                  70                  75                  80
```

```
Glu Ala Met Asp Glu Glu Ser Lys Ala Leu Lys Ala Ala Glu Lys
            85                  90                  95
Ala Asp Ala Pro
            100

<210> SEQ ID NO 12
<211> LENGTH: 2670
<212> TYPE: DNA
<213> ORGANISM: Homo sapiens

<400> SEQUENCE: 12
atgctgaaga agcagtctgc agggcttgtg ctgtggggcg ctatcctctt tgtggcctgg      60
aatgccctgc tgctcctctt cttctggacg cgcccagcac ctggcaggcc accctcagtc     120
agcgctctcg atggcgaccc cgccagcctc acccgggaag tgattcgcct ggcccaagac     180
gccgaggtgg agctggagcg gcagcgtggg ctgctgcagc agatcgggga tgccctgtcg     240
agccagcggg ggagggtgcc caccgcggcc cctcccgccc agccgcgtgt gcctgtgacc     300
cccgcgccgg cggtgattcc catcctggtc atcgcctgtg accgcagcac tgttcggcgc     360
tgcctggaca gctgctgca ttatcggccc tcggctgagc tcttccccat catcgttagc     420
caggactgcg ggcacgagga cggcccag gccatcgcct cctacggcag cgcggtcacg     480
cacatccggc agcccgacct gagcagcatt gcggtgccgc cggaccaccg caagttccag     540
ggctactaca agatcgcgcg ccactaccgc tgggcgctgg gccaggtctt ccggcagttt     600 cgcttcccccg cggccgtggt ggtggaggat gacctggagg tggccccgga cttcttcgag     660
tactttcggg ccacctatcc gctgctgaag gccgaccccct cctgtggtg cgtctcggcc     720 tggaatgaca acggcaagga gcagatggtg gacgccagca ggcctgagct gctctaccgc     780 accgacttttt tccctggcct gggctggctg ctgttggccg agctctgggc tgagctggag     840
cccaagtggc caaaggcctt ctgggacgac tggatgcggc ggccggagca gcggcagggg     900
cgggcctgca tacgccctga gatctcaaga acgatgacct ttggccgcaa gggtgtgagc     960
cacgggcagt tcttgacca gcacctcaag tttatcaagc tgaaccagca gtttgtgcac    1020
ttcacccagc tggacctgtc ttacctgcag cgggaggcct atgaccgaga tttcctcgcc    1080
cgcgtctacg tgctccccca gctgcaggtg agaaagtga ggaccaatga ccggaaggag    1140
ctgggggagg tgcgggtgca gtatacgggc agggacagct tcaaggcttt cgccaaggct    1200
ctgggtgtca tggatgacct taagtcgggg gttccgagag ctggctaccg gggtattgtc    1260
accttccagt tccggggccg ccgtgtccac ctggcgcccc caccgacgtg ggagggctat    1320
gatcctagct ggaatatgct gaagaagcag tctgcagggc ttgtgctgtg gggcgctatc    1380
ctctttgtgg cctggaatgc cctgctgctc ctcttcttct ggacgcgccc agcacctggc    1440
aggccaccct cagtcagcgc tctcgatggc gaccccgcca gcctcacccg ggaagtgatt    1500
cgcctggccc aagacgccga ggtggagctg agcggcagc gtgggctgct gcagcagatc    1560
ggggatgccc tgtcgagcca gcggggagg gtgcccaccg cggcccctcc cgcccagccg    1620
cgtgtgcctg tgaccccgc gccggcggtg attcccatcc tggtcatcgc ctgtgaccgc    1680
agcactgttc ggcgctgcct ggacaagctg ctgcattatc ggccctcggc tgagctcttc    1740
cccatcatcg ttagccagga ctgcgggcac gaggagacgg cccaggccat cgcctcctac    1800
ggcagcgcgg tcacgcacat ccggcagccc gacctgagca gcattgcggt gccgccggac    1860
caccgcaagt ccagggcta ctacaagatc gcgcgccact accgctgggc gctgggccag    1920
gtcttccggc agtttcgctt ccccgcggcc gtggtggtgg aggatgacct ggaggtggcc    1980
```

```
ccggacttct tcgagtactt tcgggccacc tatccgctgc tgaaggccga cccctccctg    2040
tggtgcgtct cggcctggaa tgacaacggc aaggagcaga tggtggacgc cagcaggcct    2100
gagctgctct accgcaccga cttttccct ggcctgggct ggctgctgtt ggccgagctc     2160
tgggctgagc tggagcccaa gtggccaaag gccttctggg acgactggat gcggcggccg    2220
gagcagcggc aggggcgggc ctgcatacgc cctgagatct caagaacgat gacctttggc    2280
cgcaagggtg tgagccacgg gcagttcttt gaccagcacc tcaagtttat caagctgaac    2340
cagcagtttg tgcacttcac ccagctggac ctgtcttacc tgcagcggga ggcctatgac    2400
cgagatttcc tcgcccgcgt ctacggtgct ccccagctgc aggtggagaa agtgaggacc    2460
aatgaccgga aggagctggg ggaggtgcgg gtgcagtata cgggcaggga cagcttcaag    2520
gctttcgcca aggctctggg tgtcatggat gaccttaagt cggggttcc gagagctggc    2580 taccggggta ttgtcacctt ccagttccgg ggccgccgtg tccacctggc gccccaccg    2640 acgtgggagg gctatgatcc tagctggaat                                    2670
```

<210> SEQ ID NO 13
<211> LENGTH: 445
<212> TYPE: PRT
<213> ORGANISM: Homo sapiens

<400> SEQUENCE: 13

```
Met Leu Lys Lys Gln Ser Ala Gly Leu Val Leu Trp Gly Ala Ile Leu
1               5                   10                  15

Phe Val Ala Trp Asn Ala Leu Leu Leu Phe Phe Trp Thr Arg Pro
                20                  25                  30

Ala Pro Gly Arg Pro Pro Ser Val Ser Ala Leu Asp Gly Asp Pro Ala
            35                  40                  45

Ser Leu Thr Arg Glu Val Ile Arg Leu Ala Gln Asp Ala Glu Val Glu
        50                  55                  60

Leu Glu Arg Gln Arg Gly Leu Leu Gln Gln Ile Gly Asp Ala Leu Ser
65                  70                  75                  80

Ser Gln Arg Gly Arg Val Pro Thr Ala Ala Pro Ala Gln Pro Arg
                85                  90                  95

Val Pro Val Thr Pro Ala Pro Ala Val Ile Pro Ile Leu Val Ile Ala
            100                 105                 110

Cys Asp Arg Ser Thr Val Arg Arg Cys Leu Asp Lys Leu Leu His Tyr
        115                 120                 125

Arg Pro Ser Ala Glu Leu Phe Pro Ile Ile Val Ser Gln Asp Cys Gly
    130                 135                 140

His Glu Glu Thr Ala Gln Ala Ile Ala Ser Tyr Gly Ser Ala Val Thr
145                 150                 155                 160

His Ile Arg Gln Pro Asp Leu Ser Ser Ile Ala Val Pro Pro Asp His
                165                 170                 175

Arg Lys Phe Gln Gly Tyr Tyr Lys Ile Ala Arg His Tyr Arg Trp Ala
            180                 185                 190

Leu Gly Gln Val Phe Arg Gln Phe Arg Phe Pro Ala Ala Val Val Val
        195                 200                 205

Glu Asp Asp Leu Glu Val Ala Pro Asp Phe Phe Glu Tyr Phe Arg Ala
    210                 215                 220

Thr Tyr Pro Leu Leu Lys Ala Asp Pro Ser Leu Trp Cys Val Ser Ala
225                 230                 235                 240

Trp Asn Asp Asn Gly Lys Glu Gln Met Val Asp Ala Ser Arg Pro Glu
```

```
                 245                 250                 255
Leu Leu Tyr Arg Thr Asp Phe Phe Pro Gly Leu Gly Trp Leu Leu
            260                 265                 270
Ala Glu Leu Trp Ala Glu Leu Glu Pro Lys Trp Pro Lys Ala Phe Trp
                275                 280                 285
Asp Asp Trp Met Arg Arg Pro Glu Gln Arg Gln Gly Arg Ala Cys Ile
            290                 295                 300
Arg Pro Glu Ile Ser Arg Thr Met Thr Phe Gly Arg Lys Gly Val Ser
305                 310                 315                 320
His Gly Gln Phe Phe Asp Gln His Leu Lys Phe Ile Lys Leu Asn Gln
                325                 330                 335
Gln Phe Val His Phe Thr Gln Leu Asp Leu Ser Tyr Leu Gln Arg Glu
            340                 345                 350
Ala Tyr Asp Arg Asp Phe Leu Ala Arg Val Tyr Gly Ala Pro Gln Leu
            355                 360                 365
Gln Val Glu Lys Val Arg Thr Asn Asp Arg Lys Glu Leu Gly Glu Val
            370                 375                 380
Arg Val Gln Tyr Thr Gly Arg Asp Ser Phe Lys Ala Phe Ala Lys Ala
385                 390                 395                 400
Leu Gly Val Met Asp Asp Leu Lys Ser Gly Val Pro Arg Ala Gly Tyr
                405                 410                 415
Arg Gly Ile Val Thr Phe Gln Phe Arg Gly Arg Val His Leu Ala
            420                 425                 430
Pro Pro Pro Thr Trp Glu Gly Tyr Asp Pro Ser Trp Asn
            435                 440                 445

<210> SEQ ID NO 14
<211> LENGTH: 4677
<212> TYPE: DNA
<213> ORGANISM: Artificial Sequence
<220> FEATURE:
<223> OTHER INFORMATION: Nucleotide sequence of plasmid pPIC6AkrecoGnTI

<400> SEQUENCE: 14 gaaattttt ttttagttt tttctcttt cagtgacctc cattgatatt taagttaata     60
aacggtcttc aatttctcaa gtttcagttt cattttcttt gttctattac aactttttt   120 acttcttgtt cattagaaag aaagcatagc aatctaatct aaggggcggt gttgacaatt  180
aatcatcggc atagtatatc ggcatagtat aatacgacaa ggtgaggaac taaaccatgg  240
ccaagccttt gtctcaagaa gaatccaccc tcattgaaag agcaacggct acaatcaaca  300
gcatccccat ctctgaagac tacagcgtcg ccagcgcagc tctctctagc gacggccgca  360
tcttcactgg tgtcaatgta tatcatttta ctggggaccc ttgtgcagaa ctcgtggtgc  420
tgggcactgc tgctgctgcg gcagctggca acctgacttg tatcgtcgcg atcggaaatg  480
agaacagggg catcttgagc ccctgcggac ggtgccgaca ggtgcttctc gatctgcatc  540
ctgggatcaa agccatagtg aaggacagtg atggacagcc gacggcagtt gggattcgtg  600
aattgctgcc ctctggttat gtgtgggagg gctaagcact cgtggccga ggagcaggac   660 tgacacgtcc gacggcggcc cacgggtccc aggcctcgga gatccgtccc ccttttcctt  720
tgtcgatatc atgtaattag ttatgtcacg cttacattca cgccctcccc ccacatccgc  780
tctaaccgaa aaggaaggag ttagacaacc tgaagtctag gtccctattt atttttttat  840
agttatgtta gtattaagaa cgttattat atttcaaatt tttctttttt ttctgtacag   900
acgcgtgtac gcatgtaaca ttatactgaa aaccttgctt gagaaggttt tgggacgctc  960
```

-continued

```
gaaggcttta atttgcaagc tggagaccaa catgtgagca aaaggccagc aaaaggccag    1020
gaaccgtaaa aaggccgcgt tgctggcgtt tttccatagg ctccgccccc ctgacgagca    1080
tcacaaaaat cgacgctcaa gtcagaggtg gcgaaacccg acaggactat aaagatacca    1140
ggcgtttccc cctggaagct ccctcgtgcg ctctcctgtt ccgaccctgc cgcttaccgg    1200
atacctgtcc gcctttctcc cttcgggaag cgtggcgctt tctcaatgct cacgctgtag    1260
gtatctcagt tcggtgtagg tcgttcgctc caagctgggc tgtgtgcacg aaccccccgt    1320
tcagcccgac cgctgcgcct tatccggtaa ctatcgtctt gagtccaacc cggtaagaca    1380
cgacttatcg ccactggcag cagccactgg taacaggatt agcagagcga ggtatgtagg    1440
cggtgctaca gagttcttga agtggtggcc taactacggc tacactagaa ggacagtatt    1500
tggtatctgc gctctgctga agccagttac cttcggaaaa agagttggta gctcttgatc    1560
cggcaaacaa accaccgctg gtagcggtgg tttttttgtt tgcaagcagc agattacgcg    1620
cagaaaaaaa ggatctcaag aagatccttt gatcttttct acggggtctg acgctcagtg    1680
gaacgaaaac tcacgttaag ggattttggt catgagatca gatctaacat ccaaagacga    1740
aaggttgaat gaaacctttt tgccatccga catccacagg tccattctca cacataagtg    1800
ccaaacgcaa caggagggga tacactagca gcagaccgtt gcaaacgcag gacctccact    1860
cctcttctcc tcaacaccca cttttgccat cgaaaaacca gcccagttat tgggcttgat    1920
tggagctcgc tcattccaat tccttctatt aggctactaa caccatgact ttattagcct    1980
gtctatcctg gcccccctgg cgaggttcat gtttgtttat ttccgaatgc aacaagctcc    2040
gcattacacc cgaacatcac tccagatgag ggctttctga gtgtggggtc aaatagtttc    2100
atgttcccca aatggcccaa aactgacagt ttaaacgctg tcttggaacc taatatgaca    2160
aaagcgtgat ctcatccaag atgaactaag tttggttcgt tgaaatgcta acggccagtt    2220
ggtcaaaaag aaacttccaa aagtcggcat accgtttgtc ttgtttggta ttgattgacg    2280
aatgctcaaa ataatctca ttaatgctta gcgcagtctc tctatcgctt ctgaaccccg    2340
gtgcacctgt gccgaaacgc aaatggggaa cacccgctt tttggatgat tatgcattgt    2400
ctccacattg tatgcttcca agattctggt gggaatactg ctgatagcct aacgttcatg    2460
atcaaaattt aactgttcta accctactt gacagcaata tataaacaga aggaagctgc    2520
cctgtcttaa acctttttt ttatcatcat tattagctta ctttcataat tgcgactggt    2580
tccaattgac aagcttttga ttttaacgac ttttaacgac aacttgagaa gatcaaaaaa    2640
caactaatta ttcgaaacga ggaattatcc atattcgcaa gcagttccac tcgaaagcat    2700
ggccctcttt ctcagtaaga gactgttgag atttaccgtc attgcaggtg cggttattgt    2760
tctcctccta acattgaatt ccaacagtag aactcagcaa tatattccga gttccatctc    2820
cgctgcattt gattttacct caggatctat atcccctgaa caacaagtca tctctgagga    2880
aaatgatgct aaaaaattag agcaaagtgc tctgaattca gaggcaagcg aagactccga    2940
agccatggat gaagaatcca aggctctgaa agctgccgct gaaaaggcag atgccccgcc    3000
ggcggtgatt cccatcctgg tcatcgcctg tgaccgcagc actgttcggc gctgcctgga    3060
caagctgctg cattatcggc cctcggctga gctcttcccc atcatcgtta gccaggactg    3120
cgggcacgag gagacggccc aggccatcgc ctcctacggc agcgcggtca cgcacatccg    3180
gcagcccgac ctgagcagca ttgcggtgcc gccggaccac gcaagttcc agggctacta    3240 caagatcgcg cgccactacc gctgggcgct gggccaggtc ttccggcagt ttcgcttccc    3300
```

-continued

```
cgcggccgtg gtggtggagg atgacctgga ggtggccccg gacttcttcg agtactttcg    3360
ggccacctat ccgctgctga aggccgaccc ctccctgtgg tgcgtctcgg cctggaatga    3420
caacggcaag gagcagatgg tggacgccag caggcctgag ctgctctacc gcaccgactt    3480
tttccctggc ctgggctggc tgctgttggc cgagctctgg gctgagctgg agcccaagtg    3540
gccaaaggcc ttctgggacg actggatgcg gcggccggag cagcggcagg ggcgggcctg    3600
catacgccct gagatctcaa gaacgatgac ctttggccgc aagggtgtga gccacgggca    3660
gttctttgac cagcacctca gtttatcaa gctgaaccag cagtttgtgc acttcaccca     3720
gctggacctg tcttacctgc agcggggagg ctatgaccga gatttcctcg cccgcgtcta    3780
cggtgctccc cagctgcagg tggagaaagt gaggaccaat gaccggaagg agctggggga    3840
ggtgcgggtg cagtatacgg gcagggacag cttcaaggct ttcgccaagg ctctgggtgt    3900
catggatgac cttaagtcgg gggttccgag agctggctac cggggtattg tcaccttcca    3960
gttccggggc cgccgtgtcc acctggcgcc cccaccgacg tgggagggct atgatcctag    4020
ctggaattag cacctgtcga ctggagacct gcaggcatgc aagcttcgac catcatcatc    4080
atcatcattg agtttgtagc cttagacatg actgttcctc agttcaagtt gggcacttac    4140
gagaagaccg gtcttgctag attctaatca agaggatgtc agaatgccat tgcctgaga    4200 gatgcaggct tcatttttga tacttttta tttgtaacct atatagtata ggatttttt     4260 tgtcattttg tttcttctcg tacgagcttg ctcctgatca gcctatctcg cagctgatga    4320
atatcttgtg gtagggtttt gggaaaatca ttcgagtttg atgttttct tggtatttcc     4380 cactcctctt cagagtacag aagattaagt gagaccttcg tttgtgcgga tcccccacac    4440
accatagctt caaaatgttt ctactccttt tttactcttc cagattttct cggactccgc    4500
gcatcgccgt accacttcaa acacccaag cacagcatac taaattttcc ctctttcttc     4560
ctctagggtg tcgttaatta cccgtactaa aggtttggaa aagaaaaaag agaccgcctc    4620
gtttcttttt cttcgtcgaa aaaggcaata aaaattttta tcacgtttct ttttctt       4677
```

<210> SEQ ID NO 15
<211> LENGTH: 33
<212> TYPE: DNA
<213> ORGANISM: Artificial Sequence
<220> FEATURE:
<223> OTHER INFORMATION: Oligonucleotide primer

<400> SEQUENCE: 15
ttcgaagctt cgctagctcg gtgtcccgat gtc                                  33

<210> SEQ ID NO 16
<211> LENGTH: 32
<212> TYPE: DNA
<213> ORGANISM: Artificial Sequence
<220> FEATURE:
<223> OTHER INFORMATION: Oligonucleotide primer

<400> SEQUENCE: 16
gaattcgaag ggaagatgag gcttcgggag cc                                   32

<210> SEQ ID NO 17
<211> LENGTH: 28
<212> TYPE: DNA
<213> ORGANISM: Artificial Sequence
<220> FEATURE:
<223> OTHER INFORMATION: Oligonucleotide primer

<400> SEQUENCE: 17

```
cgttcgcgac cggaggggcc cggccgcc                                           28

<210> SEQ ID NO 18
<211> LENGTH: 33
<212> TYPE: DNA
<213> ORGANISM: Artificial Sequence
<220> FEATURE:
<223> OTHER INFORMATION: Oligonucleotide primer

<400> SEQUENCE: 18
tcgatatcaa gcttagctcg gtgtcccgat gtc                                     33

<210> SEQ ID NO 19
<211> LENGTH: 36
<212> TYPE: DNA
<213> ORGANISM: Artificial Sequence
<220> FEATURE:
<223> OTHER INFORMATION: Oligonucleotide primer

<400> SEQUENCE: 19
gaattcgaac ttaagatggc cctctttctc agtaag                                  36

<210> SEQ ID NO 20
<211> LENGTH: 1191
<212> TYPE: DNA
<213> ORGANISM: Homo sapiens

<400> SEQUENCE: 20
atgaggcttc gggagccgct cctgagcggc gccgcgatgc aggcgcgtc cctacagcgg         60 gcctgccgcc tgctcgtggc cgtctgcgtc tggcaccttg cgtcaccct cgtttactac       120 ctggctggcc gcgacctgag ccgcctgccc caactggtcg gagtctccac accgctgcag      180
ggcggctcga acagtgccgc cgccatcggg cagtcctccg gggagctccg gaccggaggg      240 gccccggccgc cgcctcctct aggcgcctcc tcccagccgc gccgggtgg cgactccagc      300 ccagtcgtgg attctggccc tggccccgct agcaacttga cctcggtccc agtgccccac      360
accaccgcac tgtcgctgcc cgcctgccct gaggagtccc cgctgcttgt gggccccatg      420
ctgattgagt ttaacatgcc tgtggacctg agctcgtgg caaagcagaa cccaaatgtg       480
aagatgggcg ccgctatgc ccccagggac tgcgtctctc ctcacaaggt ggccatcatc       540
attccattcc gcaaccggca ggagcacctc aagtactggc tatattattt gcacccagtc      600
ctgcagcgcc agcagctgga ctatggcatc tatgttatca accaggcggg agacactata      660
ttcaatcgtg ctaagctcct caatgttggc tttcaagaag ccttgaagga ctatgactac      720
acctgctttg tgtttagtga cgtggacctc attccaatga atgaccataa tgcgtacagg      780 tgttttttcac agccacggca catttccgtt gcaatggata agtttggatt cagcctacct      840
tatgttcagt attttggagg tgtctctgct ctaagtaaac aacagtttct aaccatcaat      900
ggatttccta ataattattg gggctgggga ggagaagatg atgacatttt taacagatta      960 gttttttagag gcatgtctat atctcgccca aatgctgtgg tcgggaggtg tcgcatgatc     1020
cgccactcaa gagacaaaaa aaatgaaccc aatcctcaga ggtttgaccg aattgcacac     1080
acaaaggaga caatgctctc tgatggtttg aactcactca cctaccaggt gctggatgta     1140
cagagatacc cattgtatac ccaaatcaca gtggacatcg ggacaccgag c             1191

<210> SEQ ID NO 21
<211> LENGTH: 397
<212> TYPE: PRT
```

<213> ORGANISM: Homo sapiens

<400> SEQUENCE: 21

```
Met Arg Leu Arg Glu Pro Leu Leu Ser Gly Ala Ala Met Pro Gly Ala
1               5                   10                  15

Ser Leu Gln Arg Ala Cys Arg Leu Leu Val Ala Val Cys Val Trp His
            20                  25                  30

Leu Gly Val Thr Leu Val Tyr Tyr Leu Ala Gly Arg Asp Leu Ser Arg
        35                  40                  45

Leu Pro Gln Leu Val Gly Val Ser Thr Pro Leu Gln Gly Gly Ser Asn
    50                  55                  60

Ser Ala Ala Ile Gly Gln Ser Ser Gly Glu Leu Arg Thr Gly Gly
65                  70                  75                  80

Ala Arg Pro Pro Pro Leu Gly Ala Ser Gln Pro Arg Pro Gly
                85                  90                  95

Gly Asp Ser Ser Pro Val Val Asp Ser Gly Pro Gly Pro Ala Ser Asn
                100                 105                 110

Leu Thr Ser Val Pro Val Pro His Thr Thr Ala Leu Ser Leu Pro Ala
        115                 120                 125

Cys Pro Glu Glu Ser Pro Leu Leu Val Gly Pro Met Leu Ile Glu Phe
    130                 135                 140

Asn Met Pro Val Asp Leu Glu Leu Val Ala Lys Gln Asn Pro Asn Val
145                 150                 155                 160

Lys Met Gly Gly Arg Tyr Ala Pro Arg Asp Cys Val Ser Pro His Lys
                165                 170                 175

Val Ala Ile Ile Ile Pro Phe Arg Asn Arg Gln Glu His Leu Lys Tyr
                180                 185                 190

Trp Leu Tyr Tyr Leu His Pro Val Leu Gln Arg Gln Gln Leu Asp Tyr
            195                 200                 205

Gly Ile Tyr Val Ile Asn Gln Ala Gly Asp Thr Ile Phe Asn Arg Ala
        210                 215                 220

Lys Leu Leu Asn Val Gly Phe Gln Glu Ala Leu Lys Asp Tyr Asp Tyr
225                 230                 235                 240

Thr Cys Phe Val Phe Ser Asp Val Asp Leu Ile Pro Met Asn Asp His
                245                 250                 255

Asn Ala Tyr Arg Cys Phe Ser Gln Pro Arg His Ile Ser Val Ala Met
                260                 265                 270

Asp Lys Phe Gly Phe Ser Leu Pro Tyr Val Gln Tyr Phe Gly Gly Val
            275                 280                 285

Ser Ala Leu Ser Lys Gln Gln Phe Leu Thr Ile Asn Gly Phe Pro Asn
        290                 295                 300

Asn Tyr Trp Gly Trp Gly Gly Glu Asp Asp Asp Ile Phe Asn Arg Leu
305                 310                 315                 320

Val Phe Arg Gly Met Ser Ile Ser Arg Pro Asn Ala Val Val Gly Arg
                325                 330                 335

Cys Arg Met Ile Arg His Ser Arg Asp Lys Lys Asn Glu Pro Asn Pro
                340                 345                 350

Gln Arg Phe Asp Arg Ile Ala His Thr Lys Glu Thr Met Leu Ser Asp
            355                 360                 365

Gly Leu Asn Ser Leu Thr Tyr Gln Val Leu Asp Val Gln Arg Tyr Pro
        370                 375                 380

Leu Tyr Thr Gln Ile Thr Val Asp Ile Gly Thr Pro Ser
385                 390                 395
```

MODIFICATION OF PROTEIN GLYCOSYLATION IN METHYLOTROPHIC YEAST

FIELD OF THE INVENTION

The present invention relates to methods and genetically engineered methylotrophic yeast strains for producing glycoproteins with mammalian-like glycosylation. The present invention also relates to vectors useful for generating methylotrophic yeast strains capable of producing glycoproteins with mammalian-like glycosylation. Glycoproteins produced from the genetically engineered methylotrophic yeast strains are also provided.

BACKGROUND OF THE INVENTION

The methylotrophic yeasts including *Pichia pastoris* have been widely used for production of recombinant proteins of commercial or medical importance. However, production and medical applications of some therapeutic glycoproteins can be hampered by the differences in the protein-linked carbohydrate biosynthesis between these yeasts and the target organism such as a mammalian or human subject.

Protein N-glycosylation originates in the endoplasmic reficulum (ER), where an N-linked oligosaccharide ($Glc_3Man_9GlcNAc_2$) assembled on dolichol (a lipid carrier intermediate) is transferred to the appropriate Asn of a nascent protein. This is an event common to all eukaryotic N-linked glycoproteins. The three glucose residues and one specific α-1,2-linked mannose residue are removed by specific glucosidases and an α-1,2-mannosidase in the ER, resulting in the core oligosaccharide structure, $Man_8GlcNAc_2$. The protein with this core sugar structure is transported to the Golgi apparatus where the sugar moiety undergoes various modifications. There are significant differences in the modifications of the sugar chain in the Golgi apparatus between yeast and higher eukaryotes.

In mammalian cells, the modification of the sugar chain proceeds via 3 different pathways depending on the protein moiety to which it is added. That is, (1) the core sugar chain does not change; (2) the core sugar chain is changed by the addition of the N-acetylglucosamine-1-phosphate moiety (GlcNAc-1-P) from UDP-N-acetyl glucosamine (UDP-GlcNAc) to the 6-position of mannose in the core sugar chain, followed by removal of the GlcNAc moiety to form an acidic sugar chain in the glycoprotein; or (3) the core sugar chain is first converted into $Man_5GlcNAc_2$ as a result of the removal of 3 mannose residues by mannosidase I; and $Man_5GlcNAc_2$ is further modified by the addition of GlcNAc and the removal of two more mannose residues, followed by the sequential addition of GlcNAc, galactose (Gal), and N-acetylneuraminic acid (also called sialic acid (NeuNAc)) to form various hybrid or complex sugar chains (R. Kornfeld and S. Kornfeld, *Ann. Rev. Biochem.* 54: 631-664, 1985; Chiba et al *J. Biol. Chem.* 273: 26298-26304, 1998).

In yeast, the $Man_8GlcNAc_2$ glycans are not trimmed. The modification of the sugar chain in the Golgi apparatus involves a series of additions of mannose residues by different mannosyltransferases ("outer chain" glycosylation). The structure of the outer chain glycosylation is specific to the organisms, typically with more than 50 mannose residues in *S. cerevisiae*, and most commonly with structures smaller than $Man_{14}GlcNAc_2$ in *Pichia pastoris*. This yeast-specific outer chain glycosylation of the high mannose type is also denoted as hyperglycosylation or hypermannosylation.

Glycosylation is crucial for correct folding, stability and bioactivity of proteins. In the human body, glycosylation is partially responsible for the pharmacokinetic properties of a protein, such as tissue distribution and clearance from the blood stream. In addition, glycan structures can be involved in antigenic responses. For example, the presence of α-galactose on glycoproteins is the main reason for the immune reaction against xenografts from pig (Chen et al., *Curr Opin Chem Biol,* 3(6):650-658, 1999), while the immune reaction against glycoproteins from yeast is mainly due to the presence of α-1,3-mannose, β-linked mannose and/or phosphate residues in either a phosphomono- or phosphodiester linkage (Ballou, C. E., *Methods Enzymol,* 185:440-470, 1990; Yip et al., *Proc Natl Acad Sci USA,* 91(7):2723-2727, 1994).

Hyperglycosylation is often undesirable since it leads to heterogeneity of a recombinant protein product in both carbohydrate composition and molecular weight, which may complicate purification of the protein. The specific activity (units/weight) of hyperglycosylated enzymes can be lowered by the increased portion of carbohydrate. In addition, the outer chain glycosylation is often strongly immunogenic which may be undesirable in a therapeutic application. Moreover, the large outer chain sugar can mask the immunogenic determinants of a therapeutic protein. For example, the influenza neuraminidase (NA) expressed in *P. pastoris* is glycosylated with N-glycans containing up to 30-40 mannose residues. The hyperglycosylated NA has a reduced immunogenicity in mice, as the variable and immunodominant surface loops on top of the NA molecule are masked by the N-glycans (Martinet et al. *Eur J. Biochem.* 247: 332-338, 1997).

Therefore, it is desirable to genetically engineer methylotrophic yeast strains which produce recombinant glycoproteins having carbohydrate structures that resemble mammalian (e.g., human) carbohydrate structures.

SUMMARY OF THE INVENTION

The present invention is directed to genetically engineered methylotrophic yeast strains and methods for producing glycoproteins with mammalian-like N-glycans. The present invention is also directed to vectors and kits useful for generating the genetically engineered methylotrophic yeast strains capable of producing glycoproteins with mammalian-like N-glycans.

The term "methylotrophic yeast" as used herein includes, but is not limited to, yeast strains capable of growing on methanol, such as yeasts of the genera *Candida, Hansenula, Torulopsis,* and *Pichia.*

In one embodiment, the present invention provides a genetically engineered methylotrophic yeast strain which produces glycoproteins having a mammalian-like N-glycan structure, characterized by having five or fewer mannose residues and at least one N-acetylglucosamine residue (GlcNAc) which is linked to the core mannose-containing structure and to a terminal galactose residue.

In a preferred embodiment, the present invention provides a genetically engineered methylotrophic yeast strain which produces glycoproteins having the mammalian-like N-glycan structure, $GalGlcNAcMan_5GlcNAc_2$.

According to the present invention, the methylotrophic yeast strain which produces glycoproteins having $GalGlcNAcMan_5GlcNAc_2$ is genetically engineered to express an α-1,2-mannosidase or a functional part thereof, an N-acetylglucosaminyltransferase I (or GnTI) or a functional part thereof, and a β-1,4-galactosyltransferase (GalT) or a functional part thereof. Preferably, the methylotrophic yeast strain is also genetically engineered such that the genomic OCH1 gene is inactivated.

The α-1,2-mannosidase or a functional part thereof for expression in a genetically engineered methylotrophic yeast strain can be of an origin of any species, including mammalian species such as murine, rabbit or human, and fungal species such as *Aspergillus*, or *Trichoderma reesei*. A preferred α-1,2-mannosidase for use in the present invention is the *Trichoderma reesei* α-1,2-mannosidase. Preferably, the α-1,2-mannosidase or a functional part thereof is targeted to a site in the secretory pathway where its substrate, $Man_8GlcNAc_2$, is available. More preferably, the α-1,2-mannosidase or a functional part thereof is genetically engineered to contain an ER-retention signal and is targeted to the ER. A preferred ER-retention signal is the peptide, HDEL (SEQ ID NO: 1).

The GnTI or a functional part thereof for expression in a genetically engineered methylotrophic yeast strain can be of an origin of any species, including rabbit, rat, human, plants, insects, nematodes and protozoa such as *Leishmania tarentolae*. A preferred GnTI for use in the present invention is the human GnTI as set forth in SEQ ID NO: 13. Preferably, the GnTI or a functional part thereof is targeted to a site in the secretory pathway where its substrate, $Man_5GlcNAc_2$, is available. More preferably, the GnTI or a functional part thereof is genetically engineered to contain a Golgi-retention signal and is targeted to the Golgi apparatus. A preferred a Golgi-retention signal is the peptide as set forth in SEQ ID NO: 11, composed of the first 100 amino acids of the *Saccharomyces cerevisiae* Kre2 protein.

The GalT or a functional part thereof for expression in a genetically engineered methylotrophic yeast strain can be of an origin of any species, including human, plants (e.g. *Arabidopsis thaliana*), insects (e.g. *Drosophila melanogaster*). A preferred GalT for use in the present invention is the human GalTI as set forth in SEQ ID NO: 21. Preferably, the GalT or a functional part thereof is genetically engineered to contain a Golgi-retention signal and is targeted to the Golgi apparatus. A preferred Golgi-retention signal is the peptide as set forth in SEQ ID NO: 11, composed of the first 100 amino acids of the *Saccharomyces cerevisiae* Kre2 protein.

A methylotrophic yeast strain can be genetically engineered to express the above desired enzymes by introducing into the strain nucleotide sequences coding for these enzymes by way of, e.g., transformation. Preferably, the coding sequences are provided in vectors, each sequence placed in an operable linkage to a promoter sequence and a 3' termination sequence that are functional in the yeast strain. The vectors or linear fragments thereof are then transformed into the strain.

According to a preferred embodiment of the present invention, the methylotrophic yeast strain is also genetically engineered such that the genomic OCH1 gene is disrupted. Gene disruption can be achieved by homologous recombination between the genomic OCH1 sequence and the OCH1 sequence(s) in a knock-out vector.

In a further aspect, the present invention provides vectors useful for generating methylotrophic yeast strains which produces glycoproteins having a mammalian-like N-glycan structure.

In one embodiment, the present invention provides a "knock-in" vector which contains a nucleotide sequence coding for an enzyme to be expressed, i.e., an α-1,2-mannosidase, a GnTI, a GalT, or a functional part of any of these proteins. The coding sequence can be placed in an operable linkage to a promoter and a 3' termination sequence that are functional in the host methylotrophic yeast for expression of the encoded protein. Two or more coding sequences can be placed in the same vector for simultaneous transformation into a methylotrophic yeast strain. Preferably, the vector also includes a selectable marker gene for convenient selection of transformants. A knock-in vector can be an integrative vector or a replicative vector.

In another embodiment, the present invention provides an inactivation vector (or a "knock-out" vector) which, when introduced into a methylotrophic yeast strain, inactivates or disrupts the genomic OCH1 gene.

The OCH1 knock-out vector can include a selectable marker gene, which is operably linked, at both its 5' and 3' end, to OCH1 sequences of lengths sufficient to mediate double homologous recombination with the genomic OCH1 gene. Alternatively, an OCH1 inactivation vector can include a portion of the OCH1 gene to be disrupted, which portion encodes none or an inactive fragment of the OCH1 protein, and a selectable marker gene. The OCH1 portion is not in an operable linkage to any known promoter sequence and can, upon transformation of linear fragments of the vector, integrate into the genomic OCH1 locus by single homologous recombination. Preferably, one or more inactivating mutations, such as a stop codon or frame-shift mutation, are also introduced in the OCH1 sequence in the vector to prevent the production of any potentially active OCH1 polypeptide.

In still another aspect, the present invention provides methods of producing a glycoprotein having a mammalian-like N-glycan structure. A nucleotide sequence coding for a glycoprotein of interest can be introduced into a methylotrophic yeast strain which has been engineered to produce mammalian-like N-glycans. Alternatively, a methylotrophic yeast strain which expresses a glycoprotein of interest can be modified to express the desired enzymes (i.e., α-1,2-mannosidase, GnTI and GalT) and to inactivate the genomic OCH1 gene, in order to produce the glycoprotein with mammalian-like N-glycans.

In still another aspect, glycoproteins produced by using the methods of the present invention, i.e., glycoproteins having mammalian-like N-glycans, particularly the $GalGlcNAcMan_5GlcNAc_2$ N-glycan, are provided by the present invention.

In a further aspect, the present invention provides a kit containing one or more of the vectors of the present invention, or one or more of the genetically engineered strains of the present invention.

DETAILED DESCRIPTION OF THE INVENTION

Figure 1:
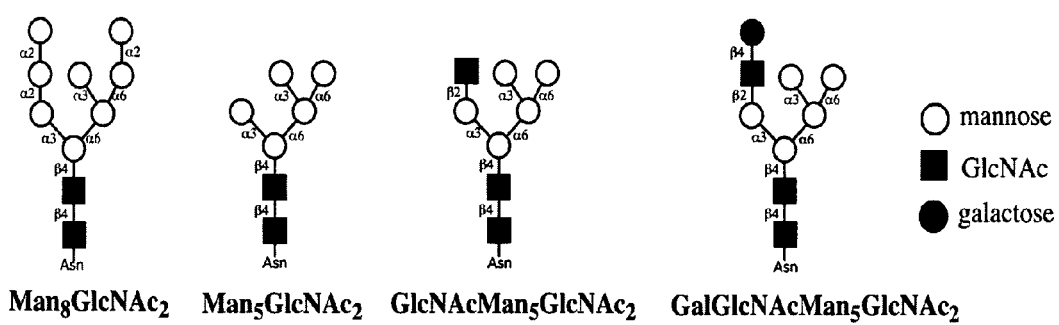
FIG. 1 depicts the structures of $M_8GlcNAc_2$, $M_5GlcNAc_2$, $GlcNAcM_5GlcNAc_2$, and $Gal\ GlcNAcM_5GlcNAc_2$.
Figure 2:
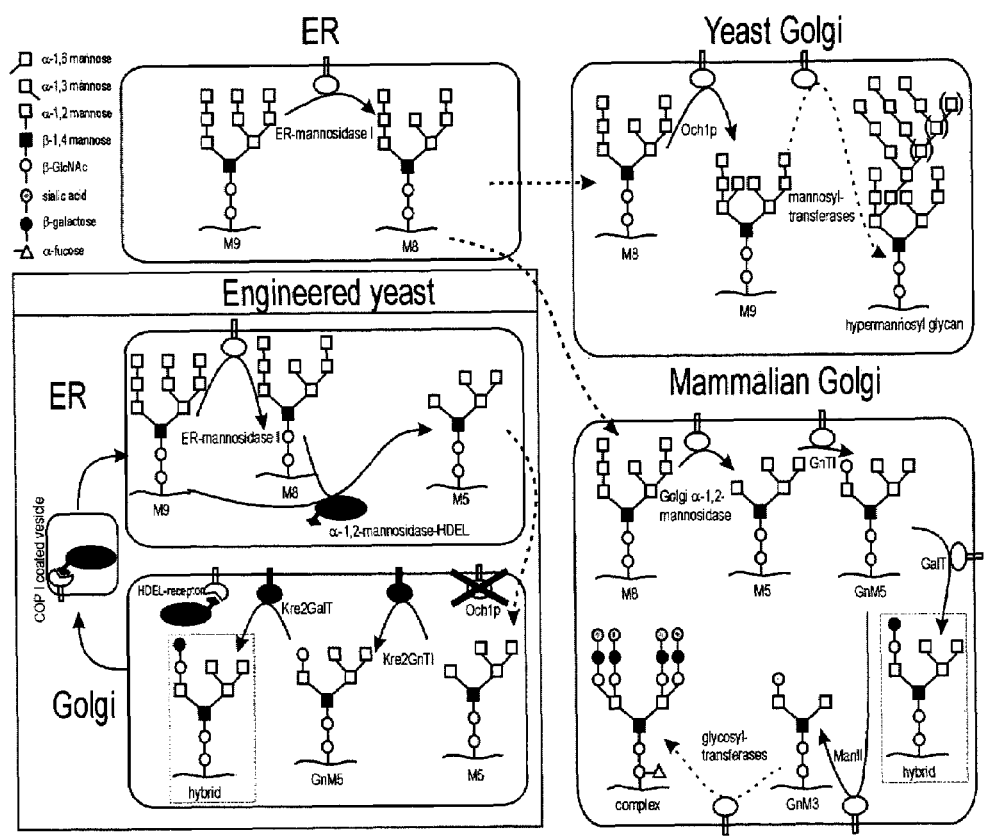
FIG. 2 graphically depicts yeast and human N-linked glycosylation and the strategy for humanization of the *Pichia pastoris* glycosylation. The glyco-engineering steps include inactivation of the α-1,6-mannosyltransferase OCH1, overexpression of a HDEL tagged α-1,2-mannosidase and Golgi-localized GnTI and GalT. The final partially obtained hybrid structure is framed.

The present invention is directed to methods, vectors and genetically engineered methylotrophic yeast strains for making recombinant glycoproteins with mammalian-like or human-like glycosylation.

By "mammalian" is meant to include any species of mammal, such as human, mice, cats, dogs, rabbits, cattle, sheep, horse and the like.

Typical complex type mammalian glycans, such as glycans produced in humans, have two to six outer branches with a sialyl-N-acetyl-lactosamine sequence linked to an inner core structure of $Man_3GlcNAc_2$. Mammalian N-glycans originate from a core oligosaccharide structure, $Man_8GlcNAc_2$, which is formed in the ER. Proteins with this core sugar structure are transported to the Golgi apparatus where $Man_9GlcNAc_2$ is converted to $Man_5GlcNAc_2$ as a result of the removal of 3 mannose residues by Golgi mannosidases I (Golgi α-1,2-mannosidases). As proteins proceed through the Golgi, $Man_5GlcNAc_2$ is further modified by the addition of GlcNAc and the removal of two more mannose residues, followed by the addition of GlcNAc, galactose (Gal), and sialic acid (SA) residues.

The term "mammalian-like glycosylation" as used herein is meant that the N-glycans of glycoproteins produced in a genetically engineered methylotrophic yeast strain include five or fewer mannose residues and are characteristic of N-glycans or intermediate carbohydrate structures in the biosynthesis of N-glycans of proteins, produced in mammalian cells such as human cells.

In a preferred embodiment, glycoproteins produced in a genetically engineered methylotrophic yeast strain of the present invention include five or fewer mannose residues, and at least one N-acetylglucosamine residue (GlcNAc) linked to the core structure containing mannose residues, and to a terminal galactose residue. For example, glycoproteins produced in a genetically engineered methylotrophic yeast strain have $GalGlcNAcMan_5GlcNAc_2$, as graphically depicted in FIG. 1. The IUPAC nomenclature of this carbohydrate ($GalGlcNAcMan_5GlcNAc_2$) is Gal(β-1,4)GlcNAc(β-1,2)Man(α-1,3){Man(α-1,3) [Man(α-1,6)]Man(α-1,6)}Man(β-1,4)GlcNAc(β-1,4)GlcNAc. Its extended nomenclature is β-D-Galp-(1→4)-β-D-GlcpNAc-(1→2)-α-D-Manp-(1→3)-{α-D-Manp-(1→3)-[α-D-Manp-(1→6)]-α-D-Manp-(1→6)}-β-D-Manp-(1→4)-β-D-GlcpNAc-(1→4)-D-GlcpNAc.

It has been established that the majority of N-glycans on glycoproteins leaving the endoplasmic reticulum (ER) of methylotrophic yeasts, including *Pichia* and especially *Pichia pastoris*, have the $Man_8GlcNAc_2$ oligosaccharide structure. After the glycoproteins are transported from the ER to the Golgi apparatus, additional mannose residues are added to this core sugar moiety by different mannosyltransferases, resulting in glycoproteins with oligosaccharide structures consisting of a high manose core, or extended, branched mannan outer chains.

According to the present invention, in order to produce recombinant glycoproteins with mammalian-like glycosylation, methylotrophic yeasts are modified to express the enzymes that convert the carbohydrate structure, $Man_8GlcNAc_2$, in a series of steps to mammalian-like N-glycans. Preferably, methylotrophic yeasts are also modified to inactivate the expression of one or more enzymes involved in the production of high mannose structures, e.g., α-1,6-mannosyltransferase encoded by the OCH1 gene.

The term "methylotrophic yeast" as used herein includes, but is not limited to, yeast strains capable of growing on methanol, such as yeasts of the genera *Candida, Hansenula, Torulopsis,* and *Pichia*. Preferred methylotrophic yeasts of the present invention are strains of the genus *Pichia*. Especially preferred are *Pichia pastoris* strains GS115 (NRRL Y-15851), GS190 (NRRL Y-18014), PPF1 (NRRL Y-18017), PPY120H, YGC4, and strains derived therefrom.

In one embodiment, the present invention provides a genetically engineered methylotrophic yeast strain which produces glycoproteins having a mammalian-like N-glycan structure, characterized as having five or fewer mannose residues and at least one N-acetylglucosamine residue (GlcNAc) which is linked to the core mannose-containing structure and to a terminal galactose residue.

In a preferred embodiment, the present invention provides a genetically engineered methylotrophic yeast strain which produces glycoproteins having the mammalian-like N-glycan structure, $GalGlcNAcMan_5GlcNAc_2$.

According to the present invention, the methylotrophic yeast strain which produces glycoproteins having $GalGlcNAcMan_5GlcNAc_2$ is genetically engineered to express an α-1,2-mannosidase or a functional part thereof, an N-acetylglucosaminyltransferase I (or GnTI) or a functional part thereof, and a β-1,4-galactosyltransferase (GalT) or a functional part thereof. Preferably, the methylotrophic yeast strain is also genetically engineered such that the genomic OCH1 gene is inactivated.

An α-1,2-mannosidase cleaves the α-1,2-linked mannose residues at the non-reducing ends of $Man_8GlcNAc_2$, and converts this core oligosaccharide on glycoproteins to $Man_5GlcNAc_2$, which is the acceptor substrate for the mammalian N-acetylglucosaminyltransferase I.

According to the present invention, a methylotrophic yeast strain can be engineered to express an α-1,2-mannosidase or a functional part thereof by introducing into the strain, e.g., by transformation, a nucleotide sequence encoding the α-1,2-mannosidase or the functional part thereof. The nucleotide sequence encoding an α-1,2-mannosidase or a functional part thereof can derive from any species. A number of α-1,2-mannosidase genes have been cloned and are available to those skilled in the art, including mammalian genes encoding, e.g., a murine α-1,2-mannosidase (Herscovics et al. *J. Biol. Chem.* 269: 9864-9871, 1994), a rabbit α-1,2-mannosidase (Lal et al. *J. Biol. Chem.* 269: 9-872-9881, 1994) or a human α-1,2-mannosidase (Tremblay et al. *Glycobiology* 8: 585-595, 1998), as well as fungal genes encoding, e.g., an *Aspergillus* α-1,2-mannosidase (msdS gene), or a *Trichoderma reesei* α-1,2-mannosidase (Maras et al. *J. Biotechnol.* 77: 255-263, 2000. Protein sequence analysis has revealed a high degree of conservation among the eukaryotic α-1,2-mannosidases identified so far.

Preferably, the nucleotide sequence for use in the present vectors encodes a fungal α-1,2-mannosidase, more preferably, a *Trichoderma reesei* α-1,2-mannosidase, and more particularly, the *Trichoderma reesei* α-1,2-mannosidase described by Maras et al. *J. Biotechnol.* 77: 255-63 (2000).

By "functional part" is meant a polypeptide fragment of an α-1,2-mannosidase which substantially retains the enzymatic activity of the full-length protein. By "substantially" is meant at least about 40%, or preferably, at least 50% or more of the enzymatic activity of the full-length α-1,2-mannosidase is retained. Characterizations of various domains, including the catalytic domain, of a number of α-1,2-mannosidases are documented. See, e.g., "Isolation of a mouse Golgi mannosidase cDNA, a member of a gene family conserved from yeast to mammals", Herscovics et al., *J Biol Chem* 269:13 9864-71 (1994); "Isolation and expression of murine and rabbit cDNAs encoding an alpha 1,2-mannosidase involved in the processing of asparagine-linked oligosaccharides", Lal et al., *J Biol Chem* 269:13 9872-81 (1994); "Molecular cloning and enzymatic characterization of a *Trichoderma reesei* 1,2-alpha-D-mannosidase", Maras M et al., *J Biotechnol* 77:255-63 (2000); and U.S. Patent Application 20020188109, incorporated herein by reference. Those skilled in the art can also readily identify and make functional parts of an α-1,2-mannosidase using a combination of techniques known in the art. The activity of a portion of an α-1,2-mannosidase of interest, expressed and purified from an appropriate expression system, can be verified using in vitro or in vivo assays described in U.S. Patent Application 20020188109, incorporated herein by reference.

In accordance with the present invention, an α-1,2-mannosidase or a functional part thereof expressed in a methylotrophic yeast strain preferably is targeted to a site in the secretory pathway where Man$_8$GlcNAc$_2$ (the substrate of α-1,2-mannosidase) is already formed on a glycoprotein, but has not reached a Golgi glycosyltransferase which elongates the sugar chain with additional mannose residues. In a preferred embodiment of the present invention, the α-1,2-mannosidase or a functional part thereof is engineered to contain an ER-retention signal such that the α-1,2-mannosidase or a functional part thereof, which is expressed in the methylotrophic yeast strain is targeted to the ER.

"An ER retention signal" refers to a peptide sequence which directs a protein having such peptide sequence to be transported to and retained in the ER. Such ER retention sequences are often found in proteins that reside and function in the ER. Multiple choices of ER retention signals are available to those skilled in the art, e.g., the first 21 amino acid residues of the *S. cerevisiae* ER protein MNS1 (Martinet et al. *Biotechnology Letters* 20: 1171-1177, 1998), and the peptide HDEL (SEQ ID NO: 1).

A preferred ER retention signal for use in the present invention is the peptide HDEL (SEQ ID NO: 1). The HDEL peptide sequence, which is found in the C-terminus of a number of yeast proteins, acts as a retention/retrieval signal for the ER (Pelham *EMBO J.* 7: 913-918, 1988). Proteins with an HDEL sequence are bound by a membrane-bound receptor (Erd2p) and then enter a retrograde transport pathway for return to the ER from the Golgi apparatus.

The α-1,2-mannosidase for use in the present invention can be further engineered, e.g., to contain an epitope tag to which antibodies are available, such as Myc, HA, FLAG and His6 tags well-known in the art. An epitope-tagged α-1,2-mannosidase can be conveniently purified, or monitored for both expression and intracellular localization.

According to the present invention, an ER retention signal can be placed, by genetic engineering, anywhere in the protein sequence of an α-1,2-mannosidase, but preferably at the C-terminus of the α-1,2-mannosidase.

An ER retention signal and an epitope tag can be readily introduced into an α-1,2-mannosidase or a functional part thereof by inserting a nucleotide sequence coding for such signal or tag into the nucleotide sequence encoding the α-1,2-mannosidase or the functional part, using any of the molecular biology techniques known in the art.

The expression of an α-1,2-mannosidase in an engineered methylotrophic yeast strain can be verified both at the mRNA level, e.g., by Northern Blot analysis, and at the protein level, e.g., by Western Blot analysis. The intracellular localization of the protein can be analyzed by using a variety of techniques, including subcellular fractionation and immunofluorescence experiments. The localization of an α-1,2-mannosidase in the ER can be determined by co-sedimentation of this enzyme with a known ER resident protein (e.g., Protein Disulfide Isomerase) in a subcellular fractionation experiment. The localization in the ER can also be determined by an immunofluorescence staining pattern characteristic of ER resident proteins, typically a perinuclear staining pattern.

To confirm that an α-1,2-mannosidase or a functional part thereof expressed in a methylotrophic yeast strain has the expected mannose-trimming activity, both in vitro and in vivo assays can be employed. Typically, an in vitro assay involves digestion of an in vitro synthesized substrate, e.g., Man$_8$GlcNAc$_2$, with the enzyme expressed and purified from a methylotrophic yeast strain, and assessing the ability of such enzyme to trim Man$_8$GlcNAc$_2$ to, e.g., Man$_5$GlcNAc$_2$. In in vivo assays, the α-1,2-mannosidase or a part thereof is co-expressed in a methylotrophic yeast with a glycoprotein known to be glycosylated with N-glycans bearing terminal α-1,2-linked mannose residues in such yeast. The enzymatic activity of such an α-1,2-mannosidase or a part thereof can be measured based on the reduction of the number of α-1,2-linked mannose residues in the structures of the N-glycans of the glycoprotein. In both in vitro and in vivo assays, the composition of a carbohydrate group can be determined using techniques that are well known in the art and are illustrated in the Examples hereinbelow.

Further according to the present invention, a methylotrophic yeast strain can be engineered to express a GlcNAc-Transferase I or a functional part thereof by introducing into the strain, e.g., by transformation, a nucleotide sequence encoding the GlcNAc-Transferase I or the functional part thereof. A GlcNAc-Transferase I is responsible for the addition of β-1,2-GlcNAc to a Man$_5$GlcNAc$_2$, and converts this core oligosaccharide on glycoproteins to GlcNAcMan$_5$GlcNAc$_2$. The mannose residues of GlcNAcMan$_5$GlcNAc$_2$ can be further trimmed by a mammalian Golgi mannosidase II, and additional sugar units, such as galactose, can be added towards forming hybrid- or complex-type sugar branches characteristic of mammalian glycoproteins.

The nucleotide sequence encoding a GlcNAc-transferase I (GnTI) or a functional part thereof for introduction into a methylotrophic yeast strain can derive from any species, e.g., rabbit, rat, human, plants, insects, nematodes and protozoa such as *Leishmania tarentolae*. Preferably, the nucleotide sequence for use in the present invention encodes a human GnTI, and more preferably, the human GnTI as set forth in SEQ ID NO: 13.

By "functional part" of a GnTI is meant a polypeptide fragment of the GnTI, which substantially retains the enzymatic activity of the full-length GnTI. By "substantially" is meant that at least about 40%, or preferably, at least 50% or more of the enzymatic activity of the full-length GnTI is retained. The enzymatic activity of a GnTI or a portion thereof can be determined by assays described in Reeves et al. (*Proc. Natl. Acad. Sci. USA*. 99(21):13419-24, 2002), Maras et al. (*Eur J. Biochem.* 249 (3):701-7, 1997), or in the Examples hereinbelow. Those skilled in the art can readily identify and make functional parts of a GnTI using a combination of techniques known in the art. For example, as illustrated by the present invention, the catalytic domain (containing the last 327 residues) of the human GnTI constitutes a "functional part" of the human GnTI.

In accordance with the present invention, a GnTI or a functional part thereof expressed in a methylotrophic yeast strain is preferably targeted to a site in the secretory pathway where $Man_5GlcNAc_2$ (the substrate of GnTI) is already formed on a glycoprotein. Preferably, the GnTI or a functional part thereof is targeted to the Golgi apparatus.

Accordingly, in a preferred embodiment of the present invention, the GnTI or a functional part thereof is engineered to contain a Golgi localization signal.

A "Golgi localization signal" as used herein refers to a peptide sequence, which directs a protein having such sequence to the Golgi apparatus of a methylotrophic yeast strain and retains the protein therein. Such Golgi localization sequences are often found in proteins that reside and function in the Golgi apparatus.

Choices of Golgi localization signals are available to those skilled in the art. A preferred Golgi localization signal for use in the present invention is a peptide derived from the N-terminal part of a *Saccharomyces cerevisiae* Kre2 protein (ScKre2); more preferably, the ScKre2 protein as set forth in SEQ ID NO: 10. A particularly preferred Golgi localization signal is the peptide (SEQ ID NO: 11), composed of amino acids 1-100 of the ScKre2 protein as set forth in SEQ ID NO: 10.

According to the present invention, a Golgi localization signal can be placed anywhere within a GnTI, but preferably at the terminus of the GnTI, and more preferably at the N-terminus of the GnTI.

The GnTI for use in the present invention can be further engineered, e.g., to contain an epitope tag to which antibodies are available, such as Myc, HA, FLAG and His6 tags, which are well-known in the art. An epitope-tagged GnTI can be conveniently purified, or monitored for both expression and intracellular localization.

A Golgi localization signal and an epitope tag can be readily introduced into a GnTI by inserting a nucleotide sequence coding for such signal or tag into the nucleotide sequence encoding the GnTI, using any of the molecular biology techniques known in the art.

Further according to the present invention, a methylotrophic yeast strain can be engineered to express a β-1,4-galactosyltransferase (GalT) of a functional part thereof by introducing into the strain, typically by transformation, a nucleotide sequence encoding the a β-1,4-galactosyltransferase (GalT) of the functional part thereof. GalT adds a β-1-4-galactose residue to the GlcNAc on the left arm of the glycan structure ($GlcNAcMan_5GlcNAc_2$), as depicted in FIG. 1.

The nucleotide sequence encoding a GalT or a functional part thereof for introduction into a methylotrophic yeast strain can derive from any species, e.g. mammalians (e.g. humans, mice), plants (e.g. *Arabidopsis thaliana*), insects (e.g. *Drosophila melanogaster*), or nematodes (e.g. *Caenorhabditis elegans*). Preferably, the nucleotide sequence for use in the present invention encodes a human GalT, and more preferably, the human GalT1 as set forth in SEQ ID NO: 21.

By "functional part" of a GalT is meant a polypeptide fragment of the GalT, which substantially retains the enzymatic activity of the full-length GalT. By "substantially" is meant that at least about 40%, or preferably, at least 50% or more of the enzymatic activity of the full-length GalT is retained. The enzymatic activity of a GalT or a portion thereof can be determined by assays described in Maras et al. (*Eur J Biochem.* 249(3):701-7, 1997) or in the Examples hereinbelow. Those skilled in the art can readily identify and make functional parts of a GalT using a combination of techniques known in the art. For example, as illustrated by the present invention, the catalytic domain of the human GalT constitutes a "functional part" of the human GalT.

In accordance with the present invention, a GalT or a functional part thereof expressed in a methylotrophic yeast strain is preferably targeted to a site in the secretory pathway where $GlcNAcMan_5GlcNAc_2$ (a substrate of GalT) is already formed on a glycoprotein. Preferably, the GalT or a functional part thereof is targeted to the Golgi apparatus.

Accordingly, in a preferred embodiment of the present invention, the GalT or a functional part thereof is engineered to contain a Golgi localization signal as described hereinabove. A preferred Golgi localization signal for targeting a GalT to the Golgi apparatus is the peptide (SEQ ID NO: 11), composed of amino acids 1-100 of the ScKre2 protein as set forth in SEQ ID NO: 10.

According to the present invention, a Golgi localization signal can be placed anywhere within a GalT, but preferably at the terminus of the GalT, and more preferably at the N-terminus of the GalT.

The GalT for use in the present invention can be further engineered, e.g., to contain an epitope tag to which antibodies are available, such as Myc, HA, FLAG and His6 tags, well-known in the art. An epitope-tagged GalT can be conveniently purified, or monitored for both expression and intracellular localization.

A Golgi localization signal and an epitope tag can be readily introduced into a GalT by inserting a nucleotide sequence coding for such signal or tag into the nucleotide sequence encoding the GalT, using any of the molecular biology techniques known in the art.

To achieve expression of a desirable protein (i.e., an α-1, 2-mannosidase, a GnTI, a GalT, or a functional part of any of these enzymes) in a methylotrophic yeast strain, the nucleotide sequence coding for the protein can be placed in a vector in an operable linkage to a promoter and a 3' termination sequence that are functional in the methylotrophic yeast strain. The vector is then introduced into the methylotrophic yeast strain, e.g., by transformation.

Promoters appropriate for expression of a protein in methylotrophic yeast include both constitutive promoters and inducible promoters. Constitutive promoters include e.g., the *Pichia pastoris* glyceraldehyde-3-phosphate dehydrogenase promoter ("the GAP promoter"). Examples of inducible promoters include, e.g., the *Pichia pastoris* alcohol oxidase I promoter ("the AOXI promoter") (U.S. Pat. No. 4,855,231), or the *Pichia pastoris* formaldehyde dehydrogenase promoter ("the FLD promoter") (Shen et al. *Gene* 216: 93-102, 1998).

3' termination sequences are sequences 3' to the stop codon of a structural gene which function to stabilize the mRNA transcription product of the gene to which the sequence is operably linked, such as sequences which elicit polyadenylation. 3' termination sequences can be obtained from *Pichia* or other methylotrophic yeasts. Examples of *Pichia pastoris* 3' termination sequences useful for the practice of the present invention include termination sequences from the AOX1 gene and the HIS4 gene.

Transformation of vectors or linear fragments thereof can be achieved using any of the known methods, such as the spheroplast technique, described by Cregg et al. (*Mol. Cell. Biol.* (12): 3376-85, 1985), or the whole-cell lithium chloride yeast transformation system, described by Ito et al. (*Agric. Biol. Chem.* 48(2):341, (1984)), modified for use in *Pichia* as described in EP 312,934. Other methods useful for transformation include those described in U.S. Pat. No. 4,929,555; Hinnen et al. (*Proc. Nat. Acad. Sci. USA* 75:1929 (1978)); Ito et al. (*J. Bacteriol.* 153:163 (1983)); U.S. Pat. No. 4,879,231; and Sreekrishna et al. (*Gene* 59:115 (1987)). Electroporation and PEG1000 whole cell transformation procedures can also be used. See Cregg and Russel, *Methods in Molecular Biology: Pichia Protocols*, Chapter 3, Humana Press, Totowa, N.J., pp. 27-39 (1998).

Transformed yeast cells can be selected by using appropriate techniques including but not limited to culturing auxotrophic cells after transformation in the absence of the biochemical product required (due to the cell's auxotrophy), selection for and detection of a new phenotype, or culturing in the presence of an antibiotic which is toxic to the yeast in the absence of a resistance gene contained in the transformants. Transformants can also be selected and/or verified by integration of the expression cassette into the genome, which can be assessed by e.g., Southern Blot or PCR analysis.

As described hereinabove, in addition to expression of an α-1,2-mannosidase, and N-acetylglucosaminyltransferase I (or GnTI), a β-1,4-galactosyltransferase (GalT), or a functional part thereof, the methylotrophic yeast strain is preferably also genetically engineered to inactivate the genomic OCH1 gene in order to efficiently produce glycoproteins having the GalGlcNAcMan$_5$GlcNAc$_2$ glycan.

The OCH1 gene encodes a membrane bound α-1,6-mannosyltransferase that is localized in the early Golgi complex and initiates the α-1,6-polymannose outer chain addition to the N-linked core oligosaccharide (Man$_5$GlcNAc$_2$ and Man$_8$GlcNAc$_2$). The *S. cerevisiae* OCH1 gene and a *Pichia* OCH1 gene have been cloned (Nakayama et al. *EMBO J.* 11: 2511-2519, 1992, and Japanese Patent Application No. 07145005, respectively). Those skilled in the art can isolate the OCH1 genes from other methylotrophic yeasts using techniques well known in the art.

According to the present invention, a disruption of the OCH1 gene of a methylotrophic yeast strain can result in either the production of an inactive protein product or no product. The disruption may take the form of an insertion of a heterologous DNA sequence into the coding sequence and/or the deletion of some or all of the coding sequence. Gene disruptions can be generated by homologous recombination essentially as described by Rothstein (in *Methods in Enzymology*, Wu et al., eds., vol 101:202-211, 1983).

To disrupt the genomic OCH1 gene by double homologous recombination, an OCH1 "knock-out" vector can be constructed, which includes a selectable marker gene, operably linked at both its 5' and 3' ends to portions of the OCH1 gene of lengths sufficient to mediate homologous recombination. The selectable marker can be one of any number of genes which either complement host cell auxotrophy or provide antibiotic resistance, including URA3, ARG4, HIS4, ADE1, LEU2 HIS3, Sh ble (*Streptoalloteichus hindustanus* bleomycin gene) and BSD (blasticidin S deaminase from *Aspergillus terreus*) genes. Other suitable selectable markers include the invertase gene from *Saccharomyces cerevisiae*, which allows methylotrophic yeasts to grow on sucrose; or the lacZ gene, which results in blue colonies due to the expression of active β-galactosidase. A linear DNA fragment of an OCH1 inactivation vector, which contains the selectable marker gene with OCH1 sequences at both its 5' and 3' end, is then introduced into host methylotrophic yeast cells using any of the transformation methods well known in the art. Integration of the linear fragment into the genomic OCH1 locus and the disruption of the OCH1 gene can be determined based on the selection marker and can be verified by, for example, Southern Blot analysis.

Alternatively, an OCH1 knock-out vector can be constructed which includes a portion of the OCH1 gene, wherein the portion is devoid of any OCH1 promoter sequence and encodes none or an inactive fragment of the OCH1 protein. By "an inactive fragment" is meant a fragment of the full-length OCH1 protein, which fragment has, preferably, less than about 10%, and more preferably, about 0% of the activity of the full-length OCH1 protein. Such portion of the OCH1 gene is inserted in a vector with no operably linkage to any promoter sequence that is functional in methylotrophic yeast. This vector can be subsequently linearized at a site within the OCH1 sequence, and transformed into a methylotrophic yeast strain using any of the transformation methods known in the art. By way of single homologous recombination, this linearized vector is then integrated in the OCH1 locus, resulting in two och1 sequences in the chromosome, neither of which is able to produce an active Och1p protein, as depicted in FIG. 3A.

Preferably, an inactivating mutation is also introduced in the och1 sequence in the vector at a site 5' to (upstream of) the linearization site and 3' to (downstream of) the translation initiation codon of OCH1. By "inactivating mutation" is meant a mutation that introduces a stop codon, a frameshift mutation or any other mutation causing a disruption of the reading frame. Such mutation can be introduced into an och1 sequence in a vector using any of the site directed mutagenesis methods known in the art. Such inactivating mutation ensures that no functional Och1p protein is formed after homologous recombination, even if there exist some promoter sequences 5' to the Och1 sequence in the knock-out vector.

The genetically engineered methylotrophic yeast strains, as described hereinabove, can be further modified if desired. For example, disruption of additional genes encoding any other *Pichia* mannosyltransferases can be made. Genes encoding enzymes that function in the mammalian glycosylation pathway, other than α-1,2-mannosidase, GnTI or GalT, can be introduced to increase the proportion of mammalian-like N-glycans and/or to further modify the mammalian-like N-glycans, if desired. For example, the genetically engineered methylotrophic yeast strains described above can be further modified to express the *S. cerevisiae* GAL10-encoded enzyme, which converts UDP-glucose into UDP-galactose and vice versa. This may increase the level of cytosolic UDP-galactose, which then stimulates the activity of GalT and increase the proportion of the GalGlcNAcM$_5$GlcNAc$_2$ glycans. In addition, the genetically engineered methylotrophic yeast strains described above can be further modified to express a mannosidase II in the Golgi, which removes additional mannose residues from GalGlcNAcM$_5$GlcNAc$_2$ thereby permitting addition of other sugar residues.

The sequence of the genetic modifications is not critical to the present invention. Introduction of nucleotide sequences encoding an α-1,2-mannosidase, a GnTI and a GalT, and disruption of the genomic OCH1 gene, can be conducted sequentially, in any order, or simultaneously by co-transformation with two or more different vectors or coding sequences or by transformation with one vector which include two or more different coding sequences.

In a further aspect, the present invention provides vectors useful for generating methylotrophic yeast strains which produce glycoproteins having a mammalian-like N-glycan structure, characterized as having five or fewer mannose residues and at least one N-acetylglucosamine residue (GlcNAc) which is linked to the core mannose-containing structure and to a terminal galactose residue, e.g., GalGlcNAcMan$_5$GlcNAc$_2$.

In one embodiment, the present invention provides a vector which contains a nucleotide sequence coding for an enzyme to be expressed, i.e., an α-1,2-mannosidase, a GnTI, a GalT, or a functional part of any of these proteins. Such vectors are also referred to as "knock-in" vectors. The coding sequence can be placed in an operable linkage to a promoter and a 3' termination sequence that are functional in the host methylotrophic yeast for expression of the encoded protein. Two or more coding sequences can be placed in the same vector for simultaneous transformation into a methylotrophic yeast strain. Preferably, the vector also includes any one of the selectable marker gene as described hereinabove for convenient selection of transformants.

According to the present invention, the knock-in vectors, which contain a sequence coding for a desirable protein to be expressed in a methylotrophic yeast strain, can be either an integrative vector or a replicative vector (such as a replicating circular plasmid). Integrative vectors are disclosed, e.g., in U.S. Pat. No. 4,882,279, which is incorporated herein by reference. Integrative vectors generally include a serially arranged sequence of at least a first insertable DNA fragment, a selectable marker gene, and a second insertable DNA fragment. The first and second insertable DNA fragments each can be about 200 nucleotides in length and have nucleotide sequences which are homologous to portions of the genomic DNA of the species to be transformed. A nucleotide sequence containing a structural gene of interest for expression is inserted in this vector between the first and second insertable DNA fragments whether before or after the marker gene. Integrative vectors can be linearized prior to yeast transformation to facilitate the integration of the nucleotide sequence of interest into the host cell genome.

In another embodiment, the present invention provides an inactivation vector (or a "knock-out" vector) which, when introduced into a methylotrophic yeast strain, inactivates or disrupts the genomic OCH1 gene.

The vector for inactivating genomic OCH1 gene can include a selectable marker gene, which is operably linked, at both its 5' and 3' end, to portions of the OCH1 gene of lengths sufficient to mediate homologous recombination, as described hereinabove. Transformation of methylotrophic yeast cells with a linear DNA fragment of such an OCH1 inactivation vector, which contains the selectable marker gene with OCH1 sequences at both its 5' and 3' end, leads to integration of the linear fragment into the genomic OCH1 locus and disruption of the genomic OCH1 gene.

Alternatively, an OCH1 inactivation vector can include a portion of the OCH1 gene to be disrupted, which portion encodes none or an inactive fragment of the OCH1 protein, and any one of the selectable marker gene as described hereinabove. Such portion of the OCH1 gene is devoid of any OCH1 promoter sequence and is not in an operable linkage to any known promoter sequence. Such vector can be linearized at a site within the Och1 sequence and subsequently transformed into a methylotrophic yeast strain, which results in inactivation of the genomic OCH1 gene by a single homologous recombination-mediated integration. Preferably, an inactivating mutation, such as a stop codon or frame-shift mutation, is also introduced in the Och1 sequence in the vector at a site 5' to (upstream of) the linearization site and 3' to (downstream of) the translation initiation codon of OCH1.

If desired, a nucleotide sequence coding for an enzyme to be expressed in a methylotrophic yeast strain can be combined with a nucleotide sequence capable of inactivating the genomic OCH1 gene, in the same vector to create a "knock-in-and-knock-out" vector.

The vectors of the present invention, including both knock-in vectors and knock-out vectors, can also contain selectable marker genes which function in bacteria, as well as sequences responsible for replication and extrachromosomal maintenance in bacteria. Examples of bacterial selectable marker genes include ampicillin resistance (Amp$^r$), tetracycline resistance (Tet$^r$), hygromycin resistance, blasticidin resistence and zeocin resistance (Zeo$^R$) genes.

Additionally, any of the above-described vectors can further include a nucleotide sequence encoding a glycoprotein of interest for expression of such glycoprotein in a methylotrophic yeast strain.

In still another aspect, the present invention provides methods of producing a glycoprotein having a mammalian-like N-glycan structure.

"A glycoprotein" as used herein refers to a protein which, in methylotrophic yeasts, is either glycosylated on one or more asparagines residues or on one or more serine or threonine residues, or on both asparagines and serine or threonine residues. Preferably, the glycoprotein is heterologous to the host methylotrophic yeast strain.

In accordance with the present invention, the production of a glycoprotein of interest with reduced glycosylation can be achieved in a number of ways. For example, a nucleotide sequence coding for a glycoprotein of interest can be introduced into a methylotrophic yeast strain which has been previously engineered to produce mammalian-like N-glycans.

The nucleotide sequence coding for a glycoprotein can be placed in an operably linkage to a promoter sequence and a 3' termination sequence that are functional in the host strain. The nucleotide sequence can include additional sequences, e.g., signal sequences coding for transit peptides when secretion of a protein product is desired. Such signal sequences are widely known, readily available and include *Saccharomyces cerevisiae* alpha mating factor prepro(αmf), the *Pichia pastoris* acid phosphatase (PHO1) signal sequence and the like.

Alternatively, a methylotrophic yeast strain which has been introduced with a coding sequence for a glycoprotein of interest, can be modified to express the desired enzymes (i.e., α-1,2-mannosidase, GnTI and GalT) and to inactivate the genomic OCH1 gene, as described hereinabove, in order to produce the glycoprotein having mammalian-like N-glycans.

Glycoproteins produced in methylotrophic yeasts can be purified by conventional methods. Purification protocols can be determined by the nature of the specific protein to be purified. Such determination is within the ordinary level of skill in the art. For example, the cell culture medium is separated from the cells and the protein secreted from the cells can be isolated from the medium by routine isolation techniques such as precipitation, immunoadsorption, fractionation or a variety of chromatographic methods.

Glycoproteins which can be produced by the methods of the present invention include bacterial, fungal or viral proteins or antigens, e.g., *Bacillus amyloliquefaciens* α-amylase, *S. cerevisiae* invertase, *Trypanosoma cruzi* trans-sialidase, HIV envelope protein, influenza virus A haemagglutinin, influenza neuraminidase, Bovine herpes virus type-1 glycoprotein D; proteins, a protein of a mammalian origin, such as human proteins, growth factors or receptors, e.g., human angiostatin, human B7-1, B7-2 and B-7 receptor CTLA-4, human tissue factor, growth factors (e.g., platelet-derived growth factor), tissue plasminogen activator, plasminogen activator inhibitor-I, urokinase, human lysosomal proteins such as α-galactosidase, plasminogen, thrombin, factor XIII; and immunoglobulins or fragments (e.g., Fab, Fab', F(ab')$_2$) of immunoglobulins. For additional useful glycoproteins which can be expressed in the genetically engineered *Pichia* strains of the present invention, see Bretthauer and Castellino, *Biotechnol. Appl. Biochem.* 30: 193-200 (1999), and Kukuruzinska et al., *Ann Rev. Biochem.* 56: 915-944 (1987).

Glycoproteins produced by using the methods of the present invention, i.e., glycoproteins having mammalian-like N-glycans, particularly the GalGlcNAcMan$_3$GlcNAc$_2$ N-glycan, are also part of the present invention.

In still another aspect, the present invention provides a kit which contains one or more of the knock-in vectors, knock-out vectors, or knock-in-and-knock-out vectors of the present invention described above.

More particularly, a kit of the present invention contains a vector having a nucleotide sequence coding for an α-mannosidase I or a functional part thereof, preferably containing an ER-rentention signal; a vector having a nucleotide sequence coding for a GnTI or a functional part thereof, preferably containing a Golgi-rentention signal; a vector having a nucleotide sequence coding for a GalT or a functional part thereof, preferably containing a Golgi-rentention signal; or a vector capable of disrupting the genomic OCH1 gene in a methylotrophic yeast, or any combinations thereof.

The kit can also include a nucleic acid molecule having a sequence coding for a heterologous glycoprotein of interest. Such nucleic acid molecule can be provided in a separate vector or in the same vector which contains sequences for knocking-in or knocking out as described hereinabove. Alternatively, the knock-in or knock-out vectors in the kit have convenient cloning sites for insertion of a nucleotide sequence encoding a heterologous protein of interest.

The kit can also include a methylotrophic yeast strain which can be transformed with any of the knock-in, knock-out or knock-in-and-knock-out vectors described hereinabove. Alternatively, the kit can include a methylotrophic yeast strain which has been engineered to produce mammalian-like N-glycans.

The present invention is further illustrated by the following examples.

EXAMPLE 1

Materials and Methods

Vector Construction and Transformation

A *Pichia pastoris* sequence was found in the GenBank under Accession No. E12456 (SEQ ID NO: 2) and was described in Japanese Patent Application No. 07145005, incorporated herein by reference. This sequence shows all typical features of an α-1,6-mannosyltransferase and is most homologous to the *S. cerevisiae* OCH1, thus referred to herein as the *Pichia pastoris* OCH1 gene. The nucleotide sequence of this *Pichia pastoris* OCH1 gene is set forth in SEQ ID NO: 2, and the amino acid sequence of the encoded protein is set forth in SEQ ID NO: 3.

The full ORF of the *Pichia pastoris* OCH1 gene was isolated by PCR using genomic DNA isolated from strain GS115 as template and the following oligonucleotides: 5'GGAAT-TCAGCATGGAGTATGGATCATGGAGTC-CGTTGGAAAGG (SEQ ID NO: 4), and 5'GCCGCTC-GAGCTAGCTTTCTTTAGTCC (SEQ ID NO: 5). The isolated OCH1 gene was cloned in pUC18 to obtain plasmid pUC18pOCH1, and the identity of the OCH1 gene sequence was confirmed by sequencing.

Plasmid pGlycoSwitchM8 (2875 bp, SEQ ID NO: 6, graphically depicted in FIG. 3A) contains a fragment of the *Pichia pastoris* OCH1 ORF encoding Ala25-Ala155, which fragment was inserted between the Bgl II and Hind III sites of pPICZB (Invitrogen, Carlsbad, Calif.). Two stop-codons were situated in frame just before codon Ala25 to prevent the possible synthesis of a truncated protein. The BstB I site of the polylinker of pPICZB was previously eliminated by filling in and religation after digestion. The unique BstB I site located inside the cloned OCH1 fragment can be used for linearization of the plasmid (See FIG. 3A for an overview of the inactivation strategy).

pGlycoSwitch M5 (5485 bp, SEQ ID NO: 9, graphically depicted in FIG. 3B) was constructed as follows. An Xba I/Cla I fragment of pPIC9 (Invitrogen, Carlsbad, Calif.), containing the *Pichia pastoris* HIS4 transcriptional terminator sequence, was inserted between the Hind III and EcoR I sites of pGlycoSwitch M8. Afterwards the 2.3 kb Bgl II/Not I fragment of pGAPZMFManHDEL (Callewaert et al., *FEBS Lett*, 503(2-3):173-178, 2001) containing the GAP promoter and preMFmannosidaseHDEL cassette, was inserted between the Hind III and Not I sites. The nucleotide sequence of the preMFmannosidaseHDEL cassette is set forth in SEQ ID NO: 8. All restriction sites used for this construction (except for the Not I site) were filled in with Klenow DNA polymerase. The unique BstB I site in pGAPZMFmanHDEL was previously eliminated by filling and religation after digestion.

In order to target the human GlcNAc-transferase I (GnTI) to the Golgi apparatus, the GnTI N-terminal part was replaced by the *S. cerevisiae* Kre2 N-terminal part that is responsible for the localization in the yeast Golgi (Lussier et al., *J Cell Biol*, 131(4):913-927, 1995). PlasmidYEp352Kre2 (provided by Dr. Howard Bussey, McGill University, Montreal, Canada) was generated by inserting the Sac I/Pvu II fragment of the Kre2 gene in theYep352 vector, which vector had been digested with Sal I (blunted with Klenow) and Sac I. YEp352Kre2 was digested with Sac I/Pvu I and made blunt by T4-polymerase. The 5'end of the Kre2 gene was isolated and cloned in a Klenow blunted SgrA I/Xba I opened pUCh-GnTI (Maras et al., *Eur J Biochem* 249(3):701-707, 1997). The fusion place between the two DNA fragments was sequenced using standard procedures. The resulting Kre2-GnTI open reading frame that contained the N-terminal part of the Kre2 gene (encoding the first 100 amino acids of the Kre2 protein, as set forth in SEQ ID NO: 11) and the catalytic domain of GnTI (the last 327 amino acids of GnTI which is as set forth in SEQ ID NO: 13) was isolated by an EcoR V/Hind III double digest and ligated in a Sal I/EcoR I opened pPIC6A vector (Invitrogen) after blunting of both fragments with Klenow polymerase. The resulting plasmid was named pPIC6AKrecoGnTI (SEQ ID NO: 14, graphically depicted in FIG. 3C). It contains the Kre2GnTI open reading frame under control of the methanol inducible AOX1 promotor and BSD gene from *A. terreus* for resistance against the antibiotic blasticidin.

Localization of GalT was achieved by fusion of the catalytic domain of GalT to the N-terminal part of Kre2p in the same way as was done to target GnTI. β-1,4-galactosyltransferase was amplified from a hepg2 cDNA library using oligonucleotides 5'TTCGAAGCTTCGCTAGCTCGGTGTC-CCGATGTC (SEQ ID NO: 15) and 5'GAATTCGAAGGGAAGATGAGGCTTCGGGAGCC (SEQ ID NO: 16) as starter sequences. The amplified fragment was cloned Hind III/EcoR I into pUC18. To omit the N-terminal 77 amino acids of the GalT protein, a PCR was performed using the following oligonucleotides as primers: 5'TTCGAAGCTTCGCTAGCTCGGTGTCCCGATGTC (SEQ ID NO: 15) and 5'CGTTCGCGACCGGAGGGGC-CCGGCCGCC (SEQ ID NO: 17). The amplified fragment was cut with Nru I/Hind III and ligated into the Hind III/SgrA I Klenow blunted pUCKreGnTI vector. The resulting Kre2-GalT fusion construct was again amplified by PCR using the as primers: 5'TCGATATCAAGCTTAGCTCGGTGTC-CCGATGTC (SEQ ID NO: 18) and 5'GAATTCGAACT-TAAGATGGCCCTCTTTCTCAGTAAG (SEQ ID NO: 19). The amplified fragment was cloned EcoR V/BstB I into the pBLURA IX (Cereghino et al., *Gene*, 263:159-169, 2001) (provided by James Cregg, Oregon Graduate Institute of Science and Technology, Beaverton, USA). Finally the URA3 gene was replaced by a Kanamycin resistance cassette by ligating a Spe I/Sma I fragment from the vector pFA6a-KanMX4 into the Spe I/Ssp I opened plasmid. The final plasmid, named as pBlKanMX4KrehGalT (SEQ ID NO: 7, graphically depicted in FIG. 3D), contained the sequence encoding a Kre2-GalT fusion protein, operably linked to the AOX1 promoter. The fusion protein was composed of the first 100 amino acids of Kre2 and the last 320 amino acids of GalT.

Transformations of these plasmids to GS115 *Pichia* strains expressing various proteins were performed as described previously (Cregg et al., *Methods in Molecular Biology*, 103:27-39, 1998). Correct genomic integration at the PpOCH1 locus was confirmed by PCR on genomic DNA.

Protein Preparation

Secreted *Trichoderma reesei* α-1,2-mannosidase was purified using a combination of HIC, anion exchange and gel filtration chromatography, as described (Maras et al., J Biotechnol, 77(2-3):255-263, 2000; Van Petegem et al., *J Mol Biol* 312(1):157-165, 2001). All SDS-PAGE experiments were done on 10% PAA gels under standard running conditions. Yeast cell wall mannoproteins were released as described by Ballou (*Methods Enzymol*, 185:440-470, 1990), which involved extensive washing of yeast cells with 0.9% NaCl in water, prolonged autoclavation of the yeast cells (90 min) in 20 mM Na-citrate after, followed by methanol precipitation (4 volumes).

N-glycan Analysis

N glycan analysis was conducted by laser-induced DNA-sequencer assisted fluorophore-assisted carbohydrate electrophoresis on the ABI 377 DNA-sequencer (DSA-FACE), as described (Callewaert et al., *Glycobiology*, 11(4):275-281, 2001). In short, glycoproteins were immobilized on a Multiscreen Immobilon-P plate and deglycosylated by PNGase treatment. N-glycans were recovered and derivatized with APTS. Excess of label was removed by size fractionation on a Sephadex G10 resin. After evaporation of the APTS-labeled oligosaccharides, a ROX-labeled GENESCAN 500 standard mixture (Applied Biosystems) was added to allow internal standardization. This mixture was run on an ABI 377A DNA sequencer (Applied Biosystems) with a 12% polyacrylamide gel in an 89 mM Tris, 89 mM borate, 2.2 mM EDTA buffer. On each gel, N-glycans of bovine RNase B and a maltodextrose ladder was run as a reference. Data analysis was performed using the GENESCAN 3.1 software (Applied Biosystems). Exoglycosidase treatment with βN-acetylhexosaminidase (Glyko) and β-galactosidase (Prozyme), was performed on labeled glycans overnight at 37° C. in 20 mM sodium acetate pH 5.5. Conventional FACE (ANTS labeling of N-glycans and electrophoresis on 30% PAA mini gels) was performed as described by Jackson (*Biochem J*, 270(3):705-713, 1990). The DSA-FACE method had a very high resolution and sensitivity, while the conventional FACE was well suited for detecting complex mixtures of higher molecular weight N-glycans ('hyperglycosylation'), which were not resolved and therefore formed a characteristic 'smear' on the gel in conventional FACE. Thus, a combination of DSA-FACE and conventional FACE analyses gave a more complete picture of the characteristics of yeast-produced glycoproteins.

Growth Curve Determination

The fresh overnight yeast cultures were diluted with fresh YPD medium to OD600 0.02 and grown overnight at 250 rpm, 30° C. (12 hours, OD 600<3.0). To start the experiment, 10 mL of fresh YPD in 50 mL polypropylene tubes were inoculated with overnight yeast cultures to get starting an OD600 value of 0.5. Aliquotes were taken every 2 hours and OD600 values were measured. All yeast strains were run at the same time in parallel.

EXAMPLE 2

Inactivation of OCH1

Disruption of the genomic *Pichia pastoris* OCH1 gene was achieved by single homologous recombination as follows. The plasmid, pGlycoSwitchM8 (FIG. 3A), was generated as described in Example 1, which included base pairs No. 73-467 of the *Pichia pastoris* OCH1gene, preceded by two in-frame non-sense codons to avoid read-through from potential earlier translation start sites in the vector. This fragment contained a centrally located BstB I site useful for linearization of the vector before transformation, and was linked at its 3' end to the AOX1 transcription terminator sequence. This vector would duplicate the OCH1 sequence present in the vector upon integration by single homologous recombination into the genomic OCH1 locus of *Pichia*. As a result, the OCH1 gene in the *Pichia* chromosome was replaced with two Och1 sequences. The first OCH1 sequence encoded a protein product of 161 amino acids long at maximum (of which 6 amino acids resulted the from the sequence in the vector), which did not include the catalytic domain of the type II transmembrane protein encoded by the full-length OCH1 gene. The second OCH1 sequence lacked the coding sequence for the first 25 amino acids of the full-length protein, and contained two in-frame stop codons that would prevent any read-through from potential upstream translation initiation sites.

Strain GS115 was transformed with the plasmid pGlycoSwitchM8. The transformant was referred to as GlycoSwitchM8 or, in short, the M8 strain or the och1 strain. PCR on genomic DNA with the primer combinations specified in FIG. 3A, showed correct integration of this construct in the expected genomic locus in about 50% of Zeocin resistant transformants, as indicated by three independent experiments.

Figure 4:
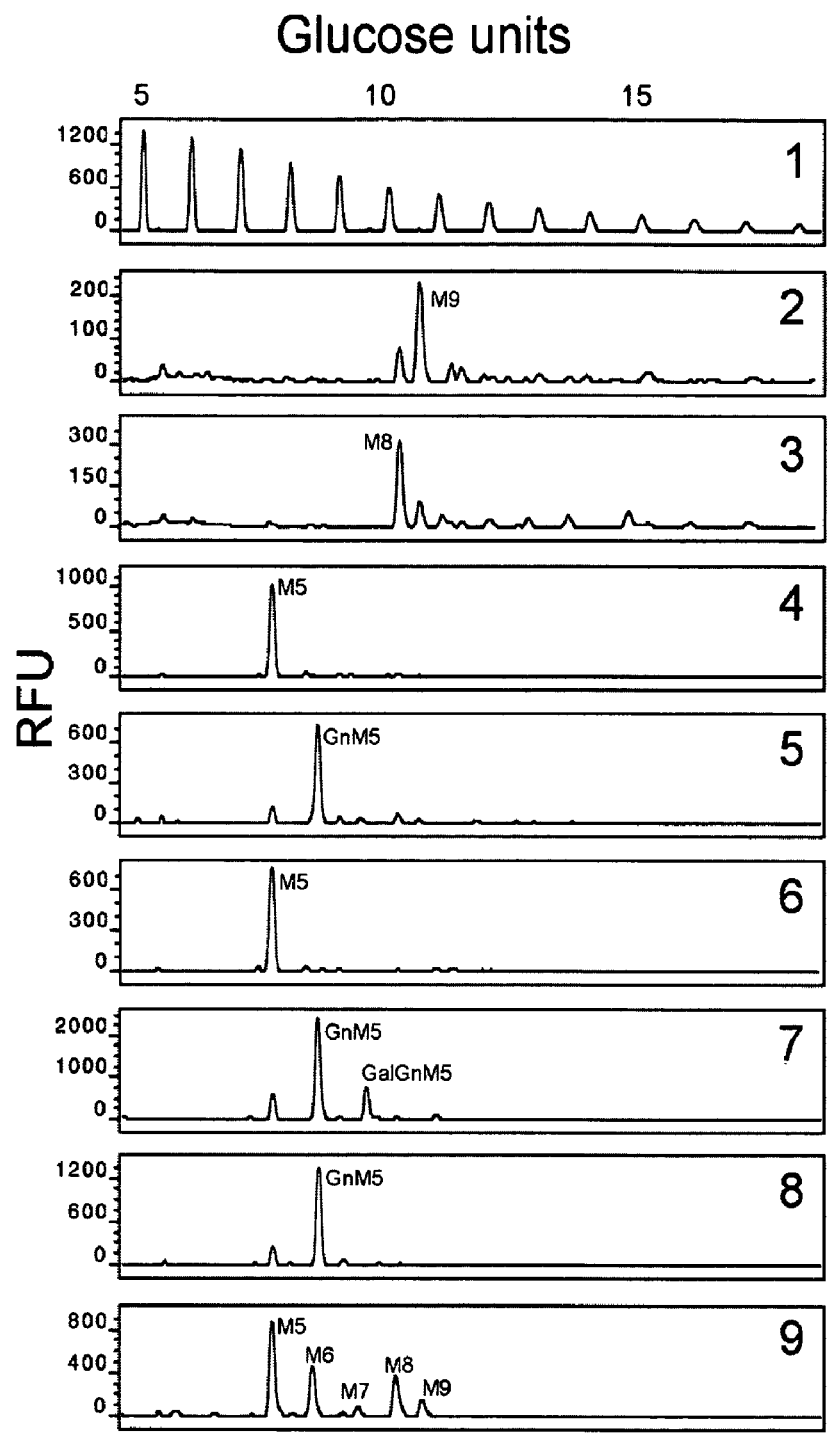
FIG. 4 graphically depicts DSA-FACE analysis of N-glycans from different glycan engineered *Pichia pastoris* strains. Panel 1: Oligomaltose reference. Panels 2-9 represent N-glycans from –2: wild type strain GS115, with $Man_9GlcNAc_2$ representing the main peak; 3: och1 inactivated strain, with $Man_8GlcNAc_2$ representing the main peak; 4: och1 inactivated ManHDEL expressing strain, with $Man_5GlcNAc_2$ representing the main peak; 5: och1 inactivated ManHDEL, KreGnTI expressing strain, with $GlcNAcMan_5GlcNAc_2$ representing the main peak; 6: same as 5 except that glycans were treated with β-N-acetylhexosaminidase, and the $GlcNAcMan_5GlcNAc_2$ peak shifted to the $Man_5GlcNAc_2$ position, indicating that terminal GlcNAc was present; 7: och1 inactivated ManHDEL, KreGnTI, KreGalT expressing strain, with the additional peak representing $GalGlcNAcMan_5GlcNAc_2$, which disappeared when treated with β-galactosidase; 9: reference glycans from bovine RNase B ($Man_{5-9}GlcNAc_2$).

Analysis of the cell wall mannoprotein N-glycans revealed a change in glycosylation pattern as can be deduced from FIG. 4. Whereas the predominant peak is Man$_9$GlcNAc$_2$ for the cell wall mannoprotein from the wild type GS115 strain, the main peak is Man$_8$GlcNAc$_2$ for the GlycoSwitchM8 strain (compare panels 2 to 3 of FIG. 4). This change in N-glycans was reverted after transformation of the M8 strain with the full-length OCH1 ORF.

Figure 5:
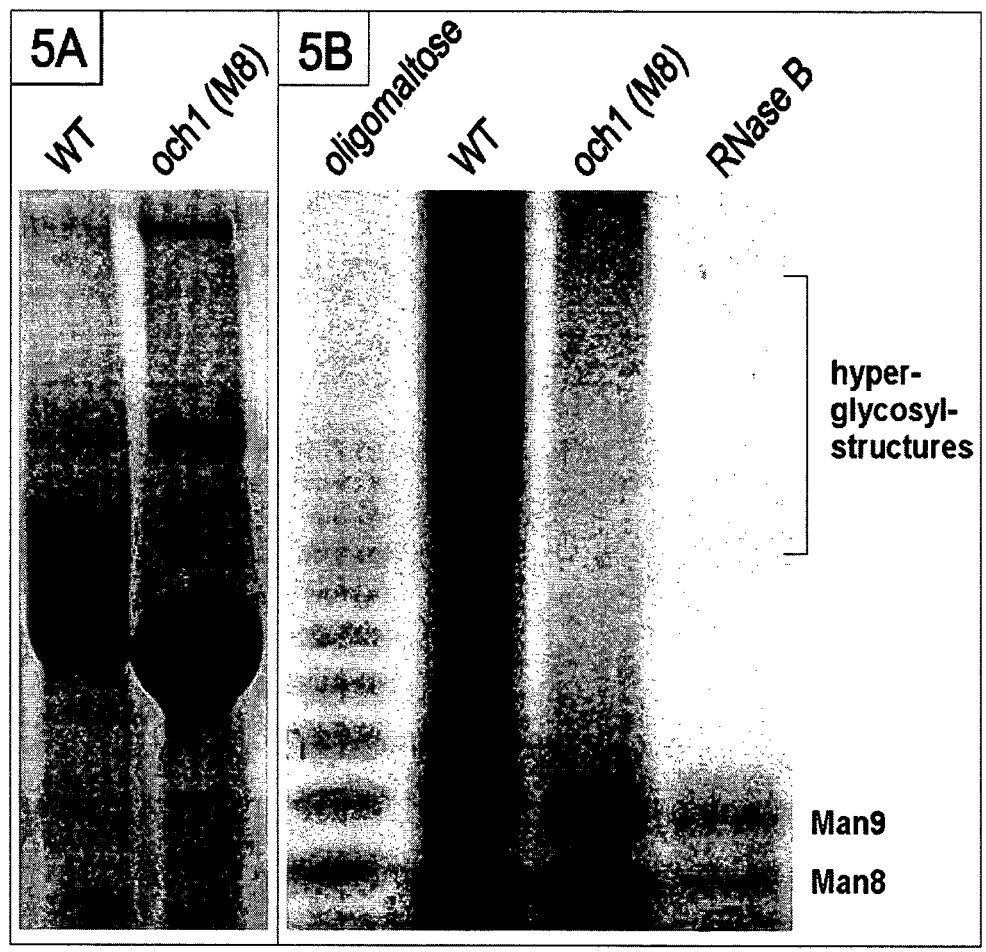
FIGS. 5A-5B demonstrate glycosylation after inactivation of *Pichia pastoris* OCH1. 5A: CBB stained SDS-PAGE gel of supernatant of *T. reesei* mannosidase secreting *Pichia pastoris* strains. In the non-engineered strain (WT) a clear smear was visible whereas this smear was absent in the och1 inactivated strain (och1 (M8)). 5B: FACE analysis of N-glycans derived from mannosidase secreted by a non-engineered strain (WT) and an och1 strain. The bands with higher electrophoretic mobility are indicated with Man8 and Man9 and represent "core" N-glycan structures.

To evaluate whether the heterogeneity of secreted glycoproteins from the M8 strain was decreased, *T. reesei* α-1,2-mannosidase, which is a typically hyperglycosylated, secreted protein in the wild type GS115 strain (Maras et al., *J Biotechnol*, 77(2-3):255-263, 2000), was analyzed using the och1 M8 strain. The culture supernatant of cells of the M8 strain, which had been transformed with a nucleotide sequence coding for *T. reesei* α-1,2-mannosidase, was separated by SDS-PAGE (FIG. 5A). The gel reveals that the smear, characteristic of hyperglycosylated proteins, was absent in the proteins produced in the GlycoSwitchM8 strain. In parallel, the secreted glycoproteins were deglycosylated by the PNGase F treatment, and the glycans were analyzed by FACE analysis on mini-gels. Typically in FACE analysis, large hyperglycosyl structures are not resolved and appear as one smearing band (FIG. 5B). The smearing band was absent with glycoproteins from the och1 strain, confirming that the heterogeneity of the N-glycans from the och1 strain was decreased.

EXAMPLE 3

Expression of ER Retained Mannosidase-HDEL

To further humanize the N-glycans of *Pichia pastoris*, ER retained *Trichoderma reesei* α-1,2-mannosidase-HDEL was expressed in the och1 strain. For easy conversion of a *Pichia pastoris* expression strain, a nucleotide sequence coding for *Trichoderma reesei* α-1,2-mannosidase-HDEL was inserted into the och1 inactivation vector. The resulting combination vector was called pGlycoSwitchM5, the construction of which is described in Example 1.

Strain GS115 was transformed with linearized pGlycoSwitchM5. Correct integration of the vector was confirmed by PCR analysis. N-glycans of mannoproteins from the transformants were analyzed by the DSA-FACE method. The glycan profile revealed a homogenous Man$_5$GlcNAc$_2$ peak (FIG. 4, panel 4). Integration of the Man$_5$GlcNAc$_2$ peak and of all the small peaks above the detection limit of this method (S/N>3) in the size area of 5 up to 25 glucose units revealed that this higher-eukaryote type high-mannose glycan made up for at least 90% of the total N-glycan pool present in this mixture.

In an alternative approach, the mannosidase-HDEL was expressed under control of the methanol inducible AOX1 promoter. No apparent differences in N-glycan profile between the two mannosidase-expressing strains (i.e. constitutive and inducible) could be detected.

To confirm the N-glycan modifications of a heterologous protein, the pGlycoSwitchM5 plasmid was transformed into a *Trypanosoma cruzi* trans-sialidase expressing *Pichia* strain as described by Laroy et al. (*Protein Expr Purif*, 20(3):389-393, 2000). Here too, Man$_5$GlcNAc$_2$ was detected on the purified protein, accounting for more than 95% of total N-glycan on the purified protein.

Growth curve analysis of the pGlycoSwitchM5 transformed strain in shake flask culture indicated that its doubling time closely mimicked that of the wild type strain. However, the engineered strain reached the stationary phase at an optical density that was about 20% lower than the wild type strain, indicating that it could be somewhat more sensitive to the stress conditions of high cell density. Nevertheless, its stress sensitivity phenotype was much less pronounced than the *S. cerevisiae* och1 strain.

EXAMPLE 4

Expression of Golgi-localized N-acetylglucosaminyltransferase I (Kre2GnTI)

To target GnTI to the Golgi, the nucleotide sequence coding for the N-terminal part of GnTI, including the cytosolic part, the transmembrane region and a part of the luminal stem region, was replaced with a nucleotide sequence coding for the *S. cerevisiae* Kre2 signal sequence. This resulted in a nucleotide sequence coding for a chimeric protein having the first 100 amino acids from Kre2p and the last 327 amino acids of GnTI.

For expression in *Pichia pastoris*, the Kre2-GnTI chimeric sequence was placed under control of the strong methanol inducible AOX1 promoter in a plasmid having the blasticidin resistance marker. The resulting construct, pPIC6KrecoGnTI (as described in Example 1), was transformed into a GS115 M5 strain after linearization in the AOX1 locus by digestion with Nsi I. The presence of the construct in the transformants was confirmed by PCR on genomic DNA using AOX1 3' and 5' primers.

N-glycans of mannoproteins of several transformants were analyzed by the DSA-FACE method. The dominant peak was about one glucose unit larger than the Man$_5$GlcNAc$_2$ peak (FIG. 4, panel 5). To determine whether this peak had terminal GlcNAc, an exoglycosidase digest was performed with β-N-acetylhexosaminidase, an enzyme that hydrolyzes β-GlcNAc linkages. Upon digestion with this enzyme, the peak shifted back to the Man$_5$GlcNAc$_2$ (FIG. 4, panel 6). This indicates that the original peak represents GlcNAcMan$_5$GlcNAc$_2$, and thus confirms the correct in vivo activity of the chimeric GnTI enzyme.

Overexpression of the Kre2GnTI chimer led to an almost complete conversion of Man$_5$GlcNAc$_2$ to GlcNAcMan$_5$GlcNAc$_2$. This suggests that enough UDP-GlcNAc donor substrate was present in the Golgi to N-acetylglucosaminylate almost all the N-glycans.

EXAMPLE 5

Expression of Golgi Retained β-1,4-galactosyltransferase

The nucleotide sequence coding for the N-terminal part of human β-1,4-galactosyltransferase 1 (the first 77 amino acids), including the transmembrane domain and the cytosolic part of the enzyme, was replaced by a nucleotide sequence coding for the *S. cerevisiae* Kre2 signal sequence. This chimeric fusion sequence was placed under control of the AOX1 promotor and the 3' end of AOX1 as a terminator. The final plasmid, pBlKanMX4KrehGalT (described in Example 1), was linearized with Pme I prior to transformation into the M5-GnTI strain.

Figure 3:
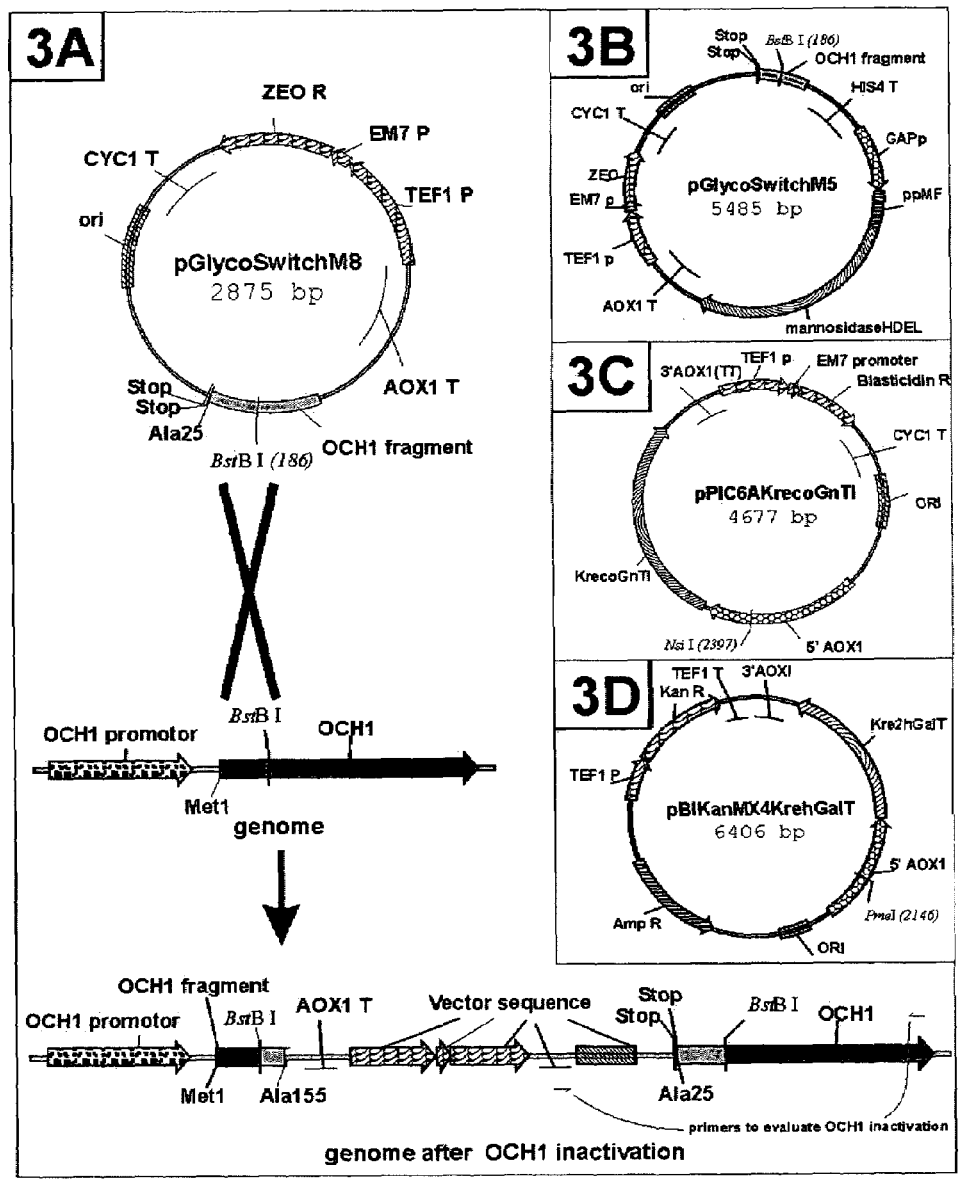
FIG. 3A graphically depicts the strategy for inactivating the genomic OCH1 gene by single homologous recombination.
FIG. 3B graphically depicts plasmid pGlycoSwitchM5 used for glycan engineering of *Pichia pastoris*. Upon linearization of pGlycoSwitchM5 with Bst BI, subsequent transformation and correct integration in the genome of *P. pastoris*, the OCH1 gene was inactivated.
FIG. 3C graphically depicts pPIC6AKrecoGnTI.
FIG. 3D graphically depicts pBlKanMX4KrehGalT.

N-glycan analysis was done with mannoproteins from several transformants. A peak about one glucose unit larger than the GlcNAcMan$_5$GlcNAc$_2$ peak was detected in the transformants, whereas the peak was absent in the non-transformed strain (FIG. 3, panel 7). The N-glycans were digested with β-galactosidase to determine whether this peak represented glycans containing terminal β-galactose. After digestion of the glycan profile, this peak shifted back to the GlcNAcMan₅GlcNAc₂ position (FIG. 4, panel 8 in comparison to panel 7). The amount of GalGlcNAcMan₅GlcNAc₂ was determined by integrating the GlcNAcMan₅GlcNAc₂ peak before and after the β-galactosidase digestion. Subtraction of these two peaks revealed that about 10% of GlcNAcMan₅GlcNAc₂ was converted to GalGlcNAcMan₅GlcNAc₂. Supplementing the medium with 0.2% galactose did not increase the amount of Gal-containing oligosaccharides.

We claim:

1. A genetically engineered *Pichia* strain, wherein said strain is engineered to express (1) a *Trichoderma reesei* α-1,2-mannosidase or a enzymatically active part thereof, (2) an N-acetylglucosaminyltransferase I (GnTI) or a enzymatically active part thereof, and (3) a β-1,4-galactosyltransferase (GalT) or a enzymatically active part thereof, and the genomic OCH1 gene of said strain is disrupted.

2. The strain of claim 1, wherein said strain is a *Pichia pastoris* strain.

3. The strain of claim 1, wherein said α-1,2-mannosidase or said enzymatically active part thereof is targeted to the ER or the Golgi of said strain.

4. The strain of claim 3, wherein said α-1,2-mannosidase or said enzymatically active part thereof is engineered to contain an ER-retention signal.

5. The strain of claim 4, wherein said ER-retention signal comprises the peptide HDEL (SEQ ID NO: 1).

6. The strain of claim 1, wherein said GnTI or said enzymatically active part thereof is of an origin of a species selected from the group consisting of rabbit, rat, human, plant, insect, nematode and protozoa.

7. The strain of claim 6, wherein said GnTI or said enzymatically active part thereof is of a human origin.

8. The strain of claim 1, wherein said GnTI or said enzymatically active part thereof is engineered to contain a Golgi-retention signal.

9. The strain of claim 8, wherein said Golgi-retention signal comprises SEQ ID NO: 11.

10. The strain of claim 1, wherein said GalT or said enzymatically active part thereof is of an origin of a species selected from the group consisting of rabbit, rat, human, plant, insect and nematode.

11. The strain of claim 10, wherein said GalT or said enzymatically active part thereof is of a human origin.

12. The strain of claim 1, wherein said GalT or said enzymatically active part thereof is engineered to contain a Golgi-retention signal.

13. The strain of claim 12, wherein said Golgi-retention signal comprises SEQ ID NO: 11.

14. The strain of claim 1, wherein said α-1,2-mannosidase or said enzymatically active part is expressed from a promoter selected from the group consisting of the AOXI promoter, the AOXII promoter, the GAP promoter, and the FLD promoter of *Pichia pastoris*.

15. The strain of claim 1, wherein said GnTI or said enzymatically active part is expressed from a promoter selected from the group consisting of the AOXI promoter, the AOXII promoter, the GAP promoter, and the FLD promoter of *Pichia pastoris*.

16. The strain of claim 1, wherein said GalT or said enzymatically active part is expressed from a promoter selected from the group consisting of the AOXI promoter, the AOXII promoter, the GAP promoter, and the FLD promoter of *Pichia pastoris*.

17. The strain of claim 1, wherein α-1,2-mannosidase or said enzymatically active part is expressed from the AOX1 promoter of *Pichia pastoris*, and said GnTI or said enzymatically active part is expressed from the GAP promoter of *Pichia pastoris*.

18. The strain of claim 1, wherein said enzymatically active part of said α-1,2-mannosidase comprises the catalytic domain of said α-1,2-mannosidase.

19. The strain of claim 1, wherein said enzymatically active part of said GnT1 comprises the catalytic domain of said GnT1.

20. The strain of claim 1, wherein said enzymatically active part of said GalT comprises the catalytic domain of said GalT.

* * * * *